United States Patent
Horn et al.

(10) Patent No.: US 6,472,522 B1
(45) Date of Patent: Oct. 29, 2002

(54) PURIFICATION OF OLIGOMERS USING DUAL-END SELECTION

(75) Inventors: Thomas Horn, Berkeley; Michael S. Urdea, Alamo, both of CA (US)

(73) Assignee: Bayer Corporation, Walpole, MA (US)

( * ) Notice: Subject to any disclaimer, the term of this patent is extended or adjusted under 35 U.S.C. 154(b) by 0 days.

(21) Appl. No.: 09/384,852

(22) Filed: Aug. 27, 1999

Related U.S. Application Data

(60) Provisional application No. 60/098,357, filed on Aug. 27, 1998.

(51) Int. Cl.$^7$ .............................................. C07H 21/00
(52) U.S. Cl. ................ 536/25.4; 536/25.33; 536/25.41; 536/25.42
(58) Field of Search .............................. 536/25.4, 25.41, 536/25.42, 25.33

(56) References Cited

U.S. PATENT DOCUMENTS

| | | |
|---|---|---|
| 4,775,619 A | * 10/1988 | Urdea |
| 5,284,933 A | 2/1994 | Döbeli et al. |
| 5,994,069 A | * 11/1999 | Hall et al. |

FOREIGN PATENT DOCUMENTS

| | | |
|---|---|---|
| WO | WO92/02528 | 2/1992 |

OTHER PUBLICATIONS

Kumar et al. (1996), "Solid Phase Synthesis and Purification of 5'-Mercaptoalkylated Oligonucleotides," *Bioorganic & Medicinal Chemistry Letters* 6(6):683–688. No Months Provided.

Olejnik et al. (1996), "Photocleavable Biotin Phosphoramidite for 5'-End-Labeling, Affinity Purification and Phosphorylation of Synthetic Oligonucleotides," *Nucleic Acids Research* 24(2):361–366. No Months Provided.

Canne et al. (1997), "Synthesis of a Versatile Purification Handle for Use with Box Chemistry Solid Phase Peptide Synthesis," *Tetrahedron Letters* 38(19):3361–3364. No Months Provided.

* cited by examiner

*Primary Examiner*—James O. Wilson
(74) *Attorney, Agent, or Firm*—Dianne E. Reed; J. Elin Hartrum

(57) ABSTRACT

Oligomers are prepared substantially free of error sequences by sequentially adding monomers to a growing chain bound to a support through a first selectably cleavable linkage, a first capture moiety and a second selectably cleavable linkage. At the completion of monomer addition, the completed oligomer is cleaved from the support to reveal the first capture moiety and purified by virtue of the presence of a second capture moiety, e.g., a terminal blocking group, and the first capture moiety. A support-bound oligomer having the structural formula (I)

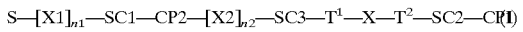

$$S-[X1]_{n1}-SC1-CP2-[X2]_{n2}-SC3-T^1-X-T^2-SC2-CP1 \quad (I)$$

is also provided wherein $T^1$, $T^2$, X1, X2, n1, n2, SC1, SC2, SC3, CP1 and CP2 are as defined herein.

16 Claims, 2 Drawing Sheets

PURIFICATION OF OLIGOMERS USING DUAL-END SELECTION

CROSS-REFERENCE TO RELATED APPLICATIONS

This application claims priority to U.S. Provisional Patent Application Ser. No. 60/098,357, filed Aug. 27, 1998.

TECHNICAL FIELD

This invention relates generally to the field of biopolymers, and more particularly relates to the purification of oligomers such as oligonucleotides, oligopeptides, oligosaccharides, and the like.

BACKGROUND OF THE INVENTION

There is an increasing demand for oligonucleotides for use in nucleic acid hybridization assays, as polymerase chain reaction ("PCR") primers or as sequencing primers in Sanger, or dideoxy, sequencing. Synthesis and purification of research-purpose quantities of oligonucleotides routinely yields product having purity of greater than 95%, but this high purity requires a lengthy, time-consuming, and labor intensive purification protocol. Typically, a 0.2 micromolescale preparation requires a seven-step purification procedure: 1) preparing a purification gel; 2) loading the gel with the reaction mixture to be purified, iii) running the gel overnight; 4) visualizing and cutting the appropriate bands from the gel; 5) soaking the bands in elution buffer for two days to extract the desired product from the gel matrix; 6) manual desalting the extracted product on a reverse phase ("RP") column and drying the solvent; and 7) manually precipitating the product from the solvent. The amount of the product obtained is quantitated using UV spectroscopy.

Any simplification of these lengthy, time consuming, and labor intensive purification protocols would be very valuable. Further, a purification scheme that could be automated and applied to oligomers other than oligonucleotides would be desirable as well.

EARLIER APPROACHES TO SIMPLIFY THE PURIFICATION OF DNA OLIGOMERS:

During the process of oligonucleotide synthesis, depurinated sites can be introduced at random sites caused by prolonged exposure to acid; the final ammonium hydroxide deprotection step cleaves the oligonucleotide chain at the depurinated sites. McHugh et al. (1995) *Nucleic Acids Research* 23:1664–1670. Methods that were devised to simplify DNA purification by, e.g., Efcavitch et al. (1985) *Nucleosides & Nucleotides* 4:267 and McBride et al. (1988) *BioTechniques* 66:362–367, were only capable of purifying shorter DNA oligomers because they did not fully account for the complicating nature of the ammonium hydroxide cleavage products.

An enzymatic purification scheme has been reported in which an oligomer is first synthesized on a solid support. Urdea et al. (1986) *Tetrahedron Lett.* 27:2933–2936. Subsequent to preparation of the desired-length solid support-bound oligonucleotide, exocyclic amines and phosphate groups in the oligomer were deprotected without cleavage of the linkage to the support. The purification used spleen phosphodiesterase to digest failure sequences that did not contain a terminal 5'-benzoyl group of the full-length oligomeric product. The process resulted in oligomers of improved purity, but abasic sites in the product oligomer remained.

A rapid cartridge purification method has also been described by Horn et al. (1988) in *Nucleic Acids Res.* 16:11559–11571. The key step in this procedure is the cleavage of all apurinic sites in the oligomer with a solution of aqueous lysine prior to removal of the crude product from the solid support. As a result, essentially all of the truncated 5'—O-dimethoxytrityl ("DMT")-containing oligomers are eliminated from the mixture of cleaved oligomers. The authors report that DNA oligomers of up to 118 bases in length were purified to near homogeneity using the procedure.

An approach related to that described in Horn et al. (1988) made use of a solid support with a disilyloxy linkage. Cleavage of abasic sites in the oligomer under very mild conditions, while the oligomer was still attached to the support, ensured that all 5'—O-DMT-containing molecules, when cleaved from the support, had correct 3'- and 5'-ends. Kwiatkowski et al. (1996) *Nucleic Acids Res.* 24:4632–4638.

Natt et al. (1997) *Tetrahedron* 53:9629–9636 describe an approach to oligomer purification that used a lipophilic capping reagent to cap failure sequences during synthesis. The lipophilic nature of the failure sequences made it possible to separate capped failure sequences from detritylated full-length oligomers chromatographically. However, the method was inefficient with respect to depurinated/cleaved sequences since the two families of species, i.e., the detritylated 5' segment and the detritylated 3' segment, do not contain the lipophilic capping group. The use of trityl groups with enhanced lipophilic properties as 5'—O protecting groups has been advocated to facilitate RP-high performance liquid chromatography ("HPLC") purification. Ramage (1993) *Tetrahedron Lett.* 34:7133–7136. As with the approaches discussed above, this process is also limited with regard to cleaved abasic sites.

Purification approaches that involve a "capture" step have been proposed. In each case, the 5' end of the oligomer to be purified carries a moiety by which capture can be effected. For example, Bannwarth et al. (1990), in *Helv. Chim. Acta* 73: 1139–114, described a combined purification/phosphorylation procedure for oligodeoxynucleotides that included a capture step. A special ribonucleotide, $N^1$—(MMT—S—$(CH_2)_{10}$)—2',3'$Bz_2$-rU-5'-$\beta$-cyanoethyl (wherein "MMT" represents monomethoxytrityl and "Bz" represents benzyl), containing a protected thiol and a diol system, was incorporated into the oligonucleotide during the final DNA synthesis cycle. After complete deprotection and removal of the MMTr protecting group, the oligomer with a 5'—SH group could be captured on a controlled pore glass ("CPG") support having surface-bound-S—S-pyridine groups; contaminating oligomers were removed by washing. The purified oligomer was released from the capture support after oxidative cleavage of the ribo-diol system and beta-elimination under basic conditions.

A purification procedure using a photolabile 5'-biotin reagent to capture oligomers on a avidin capture support has also been described. Olejnik et al. (1996) *Nucleic Acids Research* 24:361–366. The linking groups could be cleaved by photolysis to release the product oligomer in the 5'-phosphate form.

Synthesis and purification of 5'-mercaptoalkylated oligonucleotides has been described in which thiolated oligomers were purified by a single-step covalent chromatography procedure using an activated sulfhydryl support. Kumar et al. (1996) *Bioorg. Med. Chem. Lett.* 6:683–688.

In addition, purification of proteins by taking advantage of the selectivity of unique nickel-nitrilotriacetic acid ("Ni—

NTA") solid supports with an affinity tag consisting of six consecutive histidine residues has been known for years. This type of immobilized metal affinity chromatography ("IMAC") has been used for sequence-specific isolation of nucleic acids by peptide nucleic acids ("PNA")-controlled hybrid selection using oligohistidine-PNA chimera (the chemistry of PNA and peptide assembly are essentially identical). Orum et al. (1995) *BioTechniques* 19:472–480. The system has been extended to synthetic DNA oligomers containing six consecutive 6-histaminylpurine ("His") nucleotides, introduced using a convertible nucleotide phosphoramidite and further derivatized to form the His nucleotides. Min et al (1996) *Nucleic Acids Research* 24:3806–3810. The $His_6$-tagged strand was selectively retained by a Ni—NTA-agarose chromatography matrix and the captured DNA thereafter eluted from the resin.

OVERVIEW OF THE ART:

Background references that relate generally to methods for synthesizing oligonucleotides include those related to 5'- to -3' syntheses based on the use of β-cyanoethyl phosphate protecting groups, e.g., de Napoli et al. (1984) *Gazz. Chim. Ital.* 114:65, Rosenthal et al. (1983) *Tetrahedron Lett.* 24:1691, Belagaje et al. (1977) *Nucl. Acids Res.* 10:6295, and those references that describe solution-phase 5'- to -3' syntheses, such as Hayatsu et al. (1957) *J. Am. Chem. Soc.* 89:3880, Gait et al. (1977) *Nucl. Acids Res.* 4:1135, Cramer et al. (1968) *Angew. Chem. Int. Ed. Engl.* 7:473, and Blackburn et al. (1967) *J. Chem. Soc.* Part C, 2438.

In addition to the above-cited art, Matteucci et al. (1981) *J. Am. Chem. Soc.* 103:3185–3191, describes the use of phosphochloridites in the preparation of oligonucleotides. Beaucage et al. (1981) *Tetrahedron Lett.* 22:1859–1862, and U.S. Pat. No. 4,415,732 describe the use of phosphoramidites in the preparation of oligonucleotides. Smith (1983) *ABL* 15–24, the references cited therein and Warner et al. (1984) *DNA* 3:401–411 describe automated solid-phase oligodeoxyribonucleotide synthesis.

U.S. Pat. Nos. 4,483,964 and 4,517,338 to Urdea et al. describe a method for synthesizing polynucleotides by selectively introducing reagents to a solid phase substrate in a tubular reaction zone. U.S. Pat. No. 4,910,300 to Horn et al. also describes a method for synthesizing oligonucleotides by sequentially adding nucleotidic monomers to a growing chain, but involves the incorporation of labeled, $N^4$-modified cytosine residues at predetermined, spaced apart positions. U.S. Pat. No. 5,256,549 to Horn et al. describes a method for preparing oligonucleotides that involves a combination technique, i.e., in which the desired oligonucleotide is essentially synthesized and "purified" simultaneously, such that the final product is produced in substantially pure form.

Horn et al. (1986) *DNA* 5(5):421–425 describes phosphorylation of solid-supported DNA fragments using bis (cyanoethoxy)-N,N-diisopropyl-aminophosphine. See also, Horn et al. (1986) *Tetrahedron Lett.* 27:4705–4708.

Horne et al. (1990) *J. Am. Chem. Soc.* 112:2435–2437 and Froehler et al. (1992) *Biochemistry* 31:1603–1609 relate to oligonucleotide-directed triple helix formation.

U.S. Pat. Nos. 5,594,117 and 5,430,136 to Urdea et al. disclose methods and reagents, e.g., modified monomeric reagents, for synthesizing oligonucleotides containing abasic, selectably cleavable sites. Oligonucleotides prepared having such sites are selectably cleavable by photolysis or by chemical or enzymatic reagents, e.g., reducing agents.

Methods for production of oligosaccharides are known as well. For example, Kanie et al. (1992) *Curr. Opin. Struct. Biol.* 2:674–681 and Ding et al. (1995) *Adv. Exp. Med. Biol.* 376:261–269 describe chemical synthesis of oligosaccharides. In order to synthesize saccharide oligomers of defined structure, orthogonal protecting groups are provided on the hydroxyl moieties of the monosaccharides that are sequentially added to the growing oligosaccharide chain. Acetyl and benzyl protecting groups are commonly used. A saccharide moiety may become an acceptor and thus able to combine with another saccharide by replacing a hydroxyl hydrogen with, for example, p-s-φ—$CH_3$ (p-methylphenylthio), —$(CH_2)_n COOCH_3$ or —$(CH_2)_n$—O—φ—$OCH_3$. U.S. Pat. No. 4,701,494 to Graafland is also of interest as a process for the preparation of water soluble vinyl saccharide polymers is disclosed.

Accordingly, it is evident that many procedures have been developed for producing oligomers of nucleotides, amino acids, saccharides, and other monomers. These procedures for the most part rely on attaching a first monomer. Each subsequent monomeric unit is then added sequentially, with each addition involving a number of chemical reactions.

At each stage during the synthesis of the oligomer, there is a small but finite probability that a number of chains may not have been extended. Therefore, during the entire oligomerization process, a large number of errors may be introduced. These erroneous sequences (or "failure sequences") that may manifest themselves in a number of ways. Without an adequate purification process to remove failure sequences, the error may lead to undesired products, suboptimum performance, and the like.

It has therefore become of increasing importance to be able to prepare oligomers with an assurance that there is substantially no contamination with oligomers having sequences that approximate but differ from the desired sequence. By removing failure sequences at the outset, one may avoid the need for subsequent purification steps, such as electrophoresis, which can result in loss of material; loss of material can of course be a serious problem when working with very small quantities of materials.

SUMMARY OF THE INVENTION

Accordingly, it is a primary object of the invention to address the aforementioned need in the art by providing a simplified, efficient and versatile method for purifying oligomers.

It is another object of the invention to provide a such a method wherein the oligomer is an oligonucleotide, an oligopeptide, an oligosaccharide, or the like.

It is an additional object of the invention to provide such a method wherein a support-bound oligomer is purified using alternating cleavage and capture steps.

It is yet another object of the invention to provide a method of purifying a synthetic oligonucleotide by performing both a 5'-selection step and a 3'-selection step.

In one aspect of the invention, then, a method is provided for preparing an oligomer segment of interest in purified form. Initially, the method involves sequentially coupling monomers to the terminus of a growing support-bound oligomer chain until the desired support-bound oligomer is obtained. The support-bound oligomer contains a first selectably cleavable linkage, a second selectably cleavable linkage, and a third selectably cleavable linkage, wherein the oligomer segment of interest is the segment flanked by the second and third selectably cleavable linkages, and wherein a first capture moiety is present at the free terminus of the support-bound oligomer, and a second capture moiety is present between the first and third selectably cleavable linkages. The selectably cleavable linkages and the capture moieties are introduced during synthesis using techniques described herein and/or known to those of ordinary skill in the art. Following synthesis of the support-bound oligomer, the following steps are carried out to provide the oligomer segment of interest in purified form: (a) the first selectably cleavable linkage is cleaved so as to release the oligomeric product from the solid support; (b) the released oligomeric product is incubated with a first capture medium which couples to the first capture moiety, and the "captured" oligomeric product is then isolated and optionally purified; (c) the second selectably cleavable linkage is cleaved to produce the oligomer segment of interest terminating in the second capture moiety; (d) the oligomer segment provided in step (c) is incubated with a second capture medium which couples to the second capture moiety, and the captured oligomer segment is then isolated and optionally purified; and (e) the third selectably cleavable linkage is cleaved to give the oligomer segment of interest in purified form.

Another aspect of the invention relates to the support-bound oligomeric product synthesized as just described and useful as a starting material in providing the purified oligomer segment of interest. The support-bound oligomeric product has the structural formula (I)

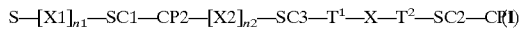

$$S-[X1]_{n1}-SC1-CP2-[X2]_{n2}-SC3-T^1-X-T^2-SC2-CP1 \quad (I)$$

wherein S represents the solid support, X1 and X2 are monomers or oligomeric segments, n1 and n2 are independently zero or 1, SC1, SC2 and SC3 represent first, second and third selectably cleavable sites, CP1 and CP2 represent first and second capture moieties, $T^1$ is the first terminus of the oligomer segment of interest X, and $T^2$ is the second terminus of the oligomer segment X. The support-bound oligomeric product of formula (I) may be used in the process described above to provide the oligomeric segment of interest X, terminating in $T^1$ and $T^2$, in purified form.

Additional objects, advantages and novel features of the invention will be set forth in part in the description which follows, and in part will become apparent to those skilled in the art upon examination of the following, or may be learned by practice of the invention.

For the sake of clarity, and without intent to limit the invention to any particular embodiment, the following discussion of the invention is related to the purification of an oligomer that is an oligonucleotide. When the oligomer is an oligonucleotide, $T^2$ and $T^1$ represent the 5' and 3' termini, respectively, SC2 represents a 5'-cleavable linkage, and SC3 represents a 3'-cleavable linkage. Those of ordinary skill in the art will recognize that, with minor modification, the methods disclosed and claimed herein can be applied to the purification of other oligomers, as well, e.g., oligopeptides, oligosaccharides and the like.

An oligonucleotide is provided having the structure of formula (I) wherein X is an oligonucleotide segment of interest and X1 and X2 are individual nucleotides or oligonucleotide segments. Purification of the oligonucleotide segment of interest is effected by cleavage at SC 1, incubation of the released product CP2—$[X2]_{n2}$—SC3—$T^1$—X—$T^2$—SC2—CP1 with a first capture medium CM1 comprised of a reverse phase chromatography or hydrophobic interaction chromatography medium, cleavage at SC2, incubation of the resulting product CP2—$[X2]_{n2}$—SC3—$T^1$—X—$T^2$ with a second capture medium CM2 comprised of a reverse phase chromatography or hydrophobic interaction chromatography medium, and cleavage at SC3 to give the purified oligonucleotide segment of interest $T^1$—X—$T^2$.

DETAILED DESCRIPTION OF THE INVENTION

Figure 1A:
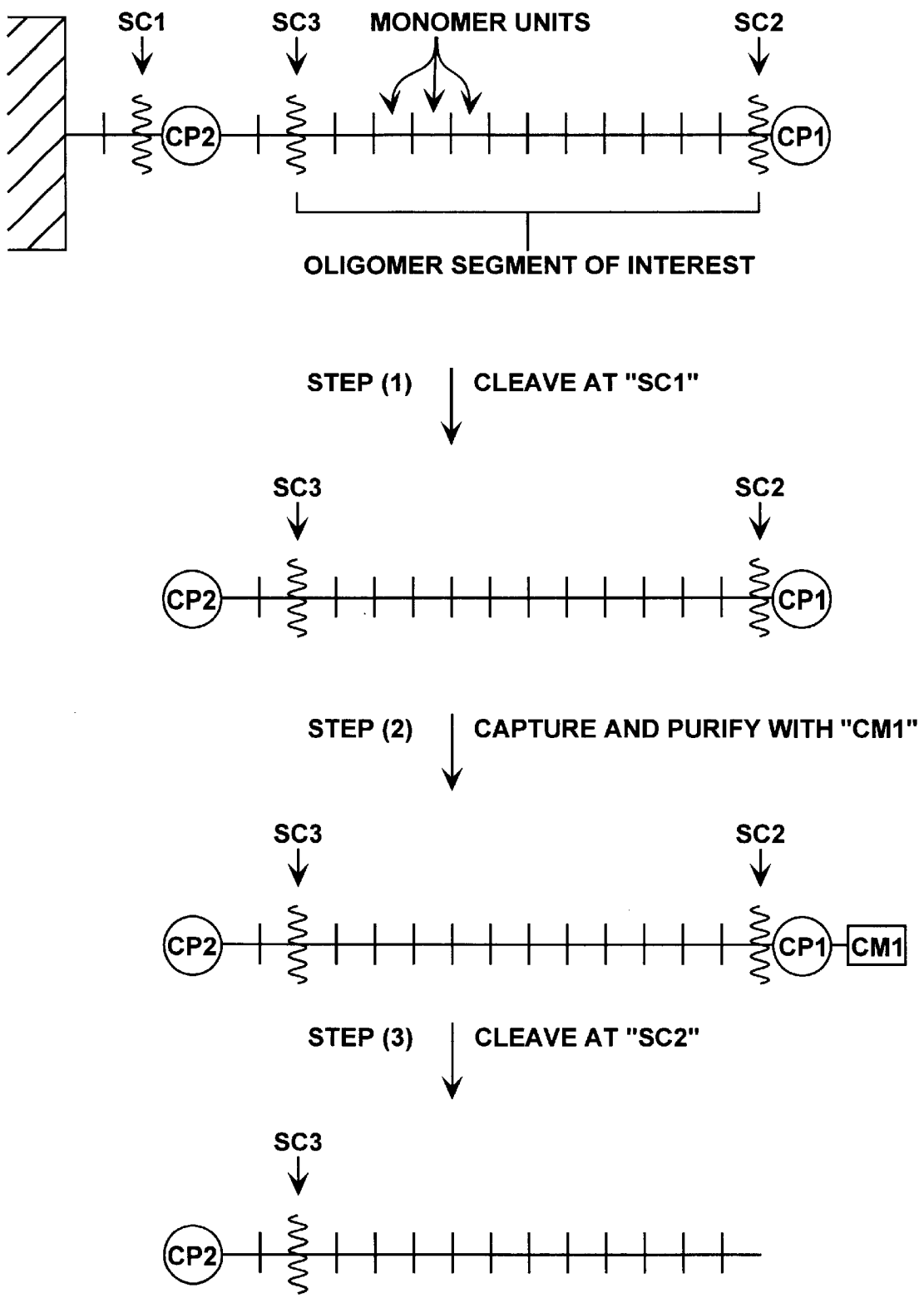
FIGS. 1A and 1B schematically illustrate purification of an oligomer segment of interest using the method of the invention.

Definitions and Nomenclature:

Before the present invention is disclosed and described in detail, it is to be understood that this invention is not limited to specific reaction conditions, materials or reagents, as such may, of course, vary. It is also to be understood that the terminology used herein is for the purpose of describing particular embodiments only and is not intended to be limiting.

Further, as used in the specification and the appended claims, the singular forms "a," "an" and "the" include plural referents unless the context clearly dictates otherwise.

In this specification and in the claims which follow, reference will be made to a number of terms which shall be defined to have the following meanings:

The term "monomer" as used herein refers to a chemical entity that can be covalently linked to one or more other such entities to form an oligomer. Examples of "monomers" include amino acids, nucleotides, saccharides, peptoids, and the like. In general, the monomers used in conjunction with the present invention have first and second sites (e.g., 5' and 3' termini, C-termini and N-termini, etc.) suitable for binding to other like monomers by means of standard chemical reactions (e.g., nucleophilic displacement of a leaving group, condensation, or the like), and a diverse element that distinguishes a particular monomer from a different monomer of the same type (e.g., a nucleotide base, an amino acid side chain, etc.). An initial support-bound "monomer" is generally used as a building block in a multi-step synthesis procedure, to form a complete oligomer, such as in the synthesis of oligonucleotides, oligopeptides, oligosaccharides, and the like.

The term "oligomer" is used herein to indicate a chemical entity that contains a plurality of monomers. As used herein, the terms "oligomer" and "polymer" are used interchangeably, as it is generally, although not necessarily, smaller "polymers" that are prepared using the method of the invention. Examples of oligomers and polymers include polydeoxyribonucleotides, polyribonucleotides, other polynucleotides that are N- or C-glycosides of a purine or pyrimidine base, polypeptides, polysaccharides, and other chemical entities that contain repeating units of like chemical structure. In the practice of the instant invention, oligomers generally comprise about 2–50 monomers, preferably about 2–20 monomers, and most preferably about 3–10 monomers.

As used herein, the terms "polynucleotide" and "oligonucleotide" shall be generic to polydeoxyribonucleotides (containing 2'-deoxy-D-ribose), polyribonucleotides (containing D-ribose), any other type of polynucleotide that is an N- or C-glycoside of a purine or pyrimidine base, and other polymers containing nonnucleotidic linkages, for example, polyamide (e.g., peptide nucleic acids ("PNAs")), polymorpholino (commercially available from the AVI Biopharm, Corvallis, Oreg., as Neugene™ polymers), and other synthetic sequence-specific nucleic acid polymers, providing that the polymers contain nucleobases in a configuration which allows for base pairing and base stacking, such as is found in DNA and RNA. There is no intended distinction in length between the term "polynucleotide" and "oligonucleotide," and these terms will be used interchangeably. These terms refer only to the primary structure of the molecule. Thus, these terms include double- and single-stranded DNA, as well as double- and single-stranded RNA, DNA:RNA hybrids, and hybrids between PNAs and DNA or RNA, and also include known types of modifications, for example, labels which are known in the art, methylation, "caps," substitution of one or more of the naturally occurring nucleotides with an analog, internucleotide modifications such as, for example, those with uncharged linkages (e.g., methyl phosphonates, phosphotriesters, phosphoramidates, carbamates, etc.), those with positively charged linkages (e.g., cationically substituted phosphoramidate linkages, as disclosed by Letsinger et al. (1988) *J. Am. Chem. Soc.* 110:4470–4471, or cationically-substituted phosphonate derivatives, as disclosed by Fathi et al. (1994) *Nucleic Acid Res.* 22:5416–5424 and Fathi et al. (1994) *Bioconjugate Chem.* 5:47–57), and those with negatively charged linkages (e.g., phosphorothioates, phosphorodithioates, etc.), those containing 2'-O-internucleotide linkages of 3'-oxy or 3'-deoxy ribose moieties, those containing pendant moieties, such as, for example, proteins (including nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide.

It will be appreciated that, as used herein, the terms "nucleoside" and "nucleotide" include those moieties which contain not only the known purine and pyrimidine bases, but also modified purine and pyrimidine bases and other heterocyclic bases which have been modified. Such modifications include methylated purines or pyrimidines, acylated purines or pyrimidines, or other heterocycles. In addition, the terms "nucleoside" and "nucleotide" include those moieties which contain not only conventional ribose and deoxyribose sugars, but also other sugars as well. Modified nucleosides or nucleotides will also include modifications on the sugar moiety, e.g., wherein one or more of the hydroxyl groups are replaced with halogen, aliphatic groups, including 2'-O-alky, e.g., 2'-O-methyl, or are functionalized as ethers, amines, or the like. Common nucleotide analogs include, but are not limited to, 1-methyladenine, 2-methyladenine, $N^6$-methyladenine, $N^6$-isopentyladenine, 2-methylthio-$N^6$-isopentyladenine, N,N-dimethyladenine, 8-bromoadenine, 2-thiocytosine, 3-methylcytosine, 5-methylcytosine, 5-ethylcytosine, 4-acetylcytosine, 1-methylguanine, 2-methylguanine, 7-methylguanine, 2,2-dimethylguanine, 8-bromoguanine, 8-chloroguanine, 8-aminoguanine, 8-methylguanine, 8-thioguanine, 5-fluorouracil, 5-bromouracil, 5-chlorouracil, 5-iodouracil, 5-ethyluracil, 5-propyluracil, 5-methoxyuracil, 5-hydroxymethyluracil, 5-(carboxyhydroxymethyl)uracil, 5-(methylaminomethyl)uracil, 5-(carboxymethylaminomethyl)-uracil, 2-thiouracil, 5-methyl-2-thiouracil, 5-(2-bromovinyl)uracil, uracil-5-oxyacetic acid, uracil-5-oxyacetic acid methyl ester, pseudouracil, 1-methylpseudouracil, queosine, inosine, 1-methylinosine, hypoxanthine, xanthine, 2-aminopurine, 6-hydroxyaminopurine, 6-thiopurine and 2,6-diaminopurine. Other suitable analogs will be known to those skilled in the art and are described in the pertinent texts and literature.

Furthermore, modifications to nucleotidic units include rearranging, appending, substituting for or otherwise altering functional groups on the purine or pyrimidine base which form hydrogen bonds to a respective complementary pyrimidine or purine. The resultant modified nucleotidic unit may form a base pair with other such modified nucleotidic units but not with A, T, C, G or U. Standard A-T and G-C base pairs form under conditions which allow the formation of hydrogen bonds between the $N^3$—H and $C^4$-oxy of thymidine and the $N^1$ and $C^6$—$NH_2$, respectively, of adenosine and between the $C^2$-oxy, $N^3$ and $C^4$—$NH_2$, of cytidine and the $C^2$—$NH_2$, $N^1$-H and $C^6$-oxy, respectively, of guanosine. Thus, for example, guanosine (2-amino-6-oxy-9-β-D-ribofuranosyl-purine) may be modified to form isoguanosine (2-oxy-6-amino-9-β-D-ribofuranosyl-purine). Such modification results in a nucleoside base which will no longer effectively form a standard base pair with cytosine. However, modification of cytosine (1-β-D-ribofuranosyl-2-oxy-4-amino-pyrimidine) to form isocytosine (1-β-D-ribofuranosyl-2-amino-4-oxy-pyrimidine) results in a modified nucleotide which will not effectively base pair with guanosine but will form a base pair with isoguanosine. Isocytosine is available from Sigma Chemical Co. (St. Louis, Mo.); isocytidine may be prepared by the method described by Switzer et al. (1993) *Biochemistry* 32:10489–10496 and references cited therein; 2'-deoxy-5-methyl-isocytidine may be prepared by the method of Tor et al. (1993) *J. Am. Chem. Soc.* 115:4461–4467 and references cited therein; and isoguanine nucleotides may be prepared using the method described by Switzer et al. (1993), supra, and Mantsch et al. (1993) *Biochem.* 14:5593–5601. The nonnatural base pairs referred to as K and 7 may be synthesized by the method described in Piccirilli et al. (1990) *Nature* 343:33–37 for the synthesis of 2,6-diaminopyrimidine and its complement (1-methylpyrazolo [4,3]pyrimidine-5,7-(4H,6H)-dione. Other such modified nucleotidic units which form unique base pairs have been described in Leach et al. (1992) *J. Am. Chem. Soc.* 114:3675–3683 and Switzer et al. (1993), supra, or will be apparent to those of ordinary skill in the art.

The designation "3'" as used in a structural representation of an internucleoside linkage refers to a bond to the 3' carbon of the ribose moiety of the nucleoside situated 5' to the linkage. Similarly, the designation "5'" as used in a structural representation of an internucleoside linkage refers to a bond to the 5' carbon of the ribose moiety of the nucleoside situated 3' to the linkage. However, as indicated above, the invention is not limited to oligonucleotides that contain only ribose moieties. One of ordinary skill in the art will recognize that the oligonucleotides herein need not be limited to traditional 3' and 5' internucleoside bonds. For example, a 2'-structural isomer of DNA containing 3'-deoxynucleosides linked through 2',5'-phosphodiester bonds has been described (Prakash et al. (1996) *Chem. Commun.* 1996:1793–1794) and such isomers are included in the definition of "oligonucleotide" herein.

A "selectably cleavable" linkage, e.g., an "abasic site," is a site in an oligonucleotide backbone that may be enzymatically, chemically or photolytically cleavable, as described in U.S. Pat. Nos. 4,775,619, 5,118,605, 5,258,506, 5,367,066, 5,380,833, 5,580,731 and 5,591,584. Abasic sites are nonnucleotidic sites as described, for example, in U.S. Pat. No. 5,430,136. By "abasic site" is meant a monomeric unit contained within an oligonucleotide chain but which does not contain a purine or pyrimidine base. The monomeric units used in conjunction with the method of the invention to provide abasic sites contain the ribose or deoxyribose ring but do not have a purine or pyrimidine base present at the 1' position. As explained in the aforementioned patents, a number of reagents and methods may be used to create abasic sites and/or sites that are cleavable using chemical reagents, restriction enzymes or photolysis. See, for example, U.S. Pat. No. 5,258,506 to Urdea et al., entitled "Photolabile Reagents for Incorporation into Oligonucleotide Chains"; U.S. Pat. No. 5,367,066 to Urdea et al., entitled "Oligonucleotides with Selectably Cleavable and/or Abasic Sites"; U.S. Pat. No. 5,380,833 to Urdea, entitled "Polynucleotide Reagents Containing Selectable Cleavage Sites"; U.S. Pat. No. 5,430,136 to Urdea et al., entitled "Oligonucleotides Having Selectably Cleavable And/or Abasic Sites"; U.S. Pat. No. 5,552,538 to Urdea et al., entitled "Oligonucleotides with Cleavable Sites"; and U.S. Pat. No. 5,578,717 to Urdea et al., entitled "Nuclotides for introducing Selectable Cleavable and/or Abasic Sites into Oligonucleotides."

As used herein, the term "amino acid" is intended to include not only the L-, D- and nonchiral forms of naturally occurring amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine), but also modified amino acids, amino acid analogs, and other chemical compounds which can be incorporated in conventional oligopeptide synthesis, e.g., D-amino acids and other unnatural or unconventional amino acids such as 4-nitrophenylalanine, isoglutamic acid, isoglutamine, ε-nicotinoyl-lysine, isonipecotic acid, tetrahydroisoquinoleic acid, α-aminoisobutyric acid, sarcosine, citrulline, cysteic acid, t-butylglycine, t-butylalanine, phenylglycine, cyclohexylalanine, β-alanine, 4-aminobutyric acid, and the like.

The terms "conventional" and "naturally occurring" as applied to oligopeptides herein refer to oligopeptides, constructed from the naturally occurring amino acids, i.e., Ala, Cys, Asp, Glu, Phe, Gly, His, Ile, Lys, Leu, Met, Asn, Pro, Gln, Arg, Ser, Thr, Val, Trp and Tyr. "Oligopeptides" refer to oligomers in which the monomers are alpha amino acids joined together through amide bonds.

The term "saccharide" is intended to include not only naturally occurring mono- and disaccharides, but also modified saccharides. Examples of monosaccharides include trioses, such as glyceraldehyde and dihydroxyacetone, tetroses, such as erythrose, erythrulose and threose, pentoses, such as ribose, ribulosem arabinose, xylose, xylulose and lyxose, hexoses, such as allose, altrose, glucose, mannose, gulose, idose, galactose, talose, psicose, fructose, sorbose, and tagatose, heptoses, such as seduheptulose, and the like. Disaccharides include dimers of the any of the above monosaccharides attached by way of α-1,2, α-1,3, α-1,4, α-1,6, β-1,2, β-1,3, β-1,4, β-1,6 linkages, or the like. Examples of such disaccharides include maltose, lactose, sucrose, and the like. Modified saccharides include those wherein one or more of the hydroxyl groups are replaced with halogen, aliphatic groups, or are functionalized as ethers, amines, phosphates, or the like. An "oligosaccharide" is an oligomer of monosaccharides. Intersugar linkages may be α-1,2, α-1,3, α-1,4, α-1,6, β-1,2, β-1,3, β-1,4, β-1,6 linkages, or the like.

"Molecular mimetics" include, but are not limited to, small organic compounds; nucleic acids and nucleic acid derivatives; saccharides and oligosaccharides; peptide mimetics including peptides, proteins, and derivatives thereof, such as peptides containing non-peptide organic moieties, synthetic peptides that may or may not contain amino acids or peptide bonds but retain the structural and functional features of a peptide ligand; and peptoids and oligopeptoids such as those described by Simon et al. (1992); *Proc. Natl. Acad. Sci. USA* 89:9367; and antibodies, including anti-idiotype antibodies.

A "peptoid" is an oligomer made up, at least in part, of monomer units of amino acid "substitutes" comprised of any molecule other than an amino acid, but which serves to mimic an amino acid in the peptoid polymer. Particularly preferred monomer units are N-alkylated derivatives of glycine. Peptoids are produced by linking the amino acid "substitute" into a linear chain or cyclic structure with amino acids and/or other amino acid substitutes. The links may include, without limitation, peptide bonds, esters, ethers, amines, phosphates, sulfates, sulfites, thioethers, thioesters, aliphatic bonds, and carbamates. Examples of amino acid substitutes include, without limitation, N-substituted glycine, N-alkylated glycines, N-substituted alanine, N-substituted D-alanine, urethanes, and substituted hydroxy acids such as hydroxyacetic acid, 2-hydroxypropanoic acid, 3-hydroxypropanoic acid, 3-phenyl-2-hydroxypropanoic acid, and the like. A peptoid may comprise amino acid substitutes using more than one type of link provided that the chemistry for the reaction schemes are compatible and encompassed generally by the reactions described herein. Other examples of amino acid substitutes and peptoids are described, for example, in Bartlett et al., PCT WO91/19735 and Zuckermann et al., PCT WO94/06451.

By "protecting group" or "PG" as used herein is meant a species that prevents a segment of a molecule or the site to which the protecting group is attached from undergoing a specific chemical reaction, but which is removable from the molecule following completion of that reaction. This is in contrast to a "capping group," which also forms a covalent bond with a segment of a molecule but prevents any further chemical transformation of that segment.

The terms "protection" and "deprotection" as used herein relate, respectively, to the addition and removal of chemical protecting groups using conventional materials and techniques within the skill of the art and/or described in the pertinent literature; see, for example, Greene et al., *Protective Groups in Organic Sythesis*, 2nd Ed. (New York: John Wiley & Sons, 1991). Suitable methods for removing hydroxyl protecting groups, in particular, include, but are not limited to, treatment with an acid of sufficient strength to remove the protecting group but which will not otherwise alter the properties of the solid support or any components bound thereto.

The term "alkyl" as used herein, unless otherwise specified, refers to a saturated straight chain, branched or cyclic hydrocarbon group of 1 to 24, typically 1–12, carbon atoms, such as methyl, ethyl, n-propyl, isopropyl, n-butyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl. The term "lower alkyl" intends an alkyl group of 1 to 6 carbon atoms, and includes, for example, methyl, ethyl, n-propyl, isopropyl, n-butyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl. The term "cycloalkyl" refers to cyclic alkyl groups such as cyclopropyl, cyclobutyl, cyclopentyl, cyclohexyl, cycloheptyl and cyclooctyl.

The term "alkenyl" as used herein, unless otherwise specified, refers to a branched, unbranched or cyclic (in the case of $C_5$ and $C_6$) hydrocarbon group of 2 to 24, typically 2 to 12, carbon atoms containing at least one double bond, such as ethenyl, vinyl, allyl, octenyl, decenyl, and the like. The term "lower alkenyl" intends an alkenyl group of 2 to 6 carbon atoms, and includes, for example, vinyl and allyl. The term "cycloalkenyl" refers to cyclic alkenyl groups.

The term "aryl" as used herein refers to an aromatic species containing 1 to 5 aromatic rings, either fused or linked, and either unsubstituted or substituted with 1 or more substituents typically selected from the group consisting of amino, halogen and lower alkyl. Preferred aryl substituents contain 1 to 3 fused aromatic rings, and particularly preferred aryl substituents contain 1 aromatic ring or 2 fused aromatic rings. Aromatic groups herein may or may not be heterocyclic.

The term "arylene" refers to a bifunctional group wherein aryl is as defined above.

The terms "aralkyl" and "alkaryl" refer to moieties containing both alkyl and aryl species, typically containing less than about 24 carbon atoms, and more typically less than about 12 carbon atoms in the alkyl segment of the moiety, and typically containing 1 to 5 aromatic rings. The term "aralkyl" refers to an aryl-substituted alkyl group, while the term "alkaryl" refers to an alkyl-substituted aryl group. The terms "aralkylene"and "alkarylene" are used in a similar manner to refer to moieties containing both alkylene and aryl species, typically containing less than about 24 carbon atoms in the alkylene portion and 1 to 5 aromatic rings in the aryl portion; "aralkylene" refers to an aryl-substituted alkylene linkage, while "alkarylene" refers to an alkyl-substituted arylene linkage.

The term "heterocyclic" refers to a five- or six-membered monocyclic structure or to an eight- to eleven-membered bicyclic structure which is either saturated or unsaturated. The heterocyclic groups herein may be aliphatic or aromatic. Each heterocycle consists of carbon atoms and from one to four heteroatoms selected from the group consisting of nitrogen, oxygen and sulfur. As used herein, the terms "nitrogen heteroatoms" and "sulfur heteroatoms" include any oxidized form of nitrogen and sulfur, and the quaternized form of any basic nitrogen. Examples of heterocycles include, but are not limited to, pyrrole, pyrrolidine, pyridine, piperidine, morpholine, quinoline, indole, pyrimidine, piperazine, pipecoline, imidazole, benzimidazole, purine and the like. These groups may also be substituted as outlined above. "Purified" or "homogeneous," when referring to an oligomer sequence, indicates that the oligomer is present in the substantial absence of other biological macromolecules of the same type or stereoisomeric configuration. The term "purified" as in a "purified oligomer segment of interest" refers to a composition in which the oligomer segment of interest represents at least about 90 wt. %, preferably at least about 95 wt. %, and most preferably at least about 95 wt. % of the composition.

The terms "halo" or "halogen" are used in their conventional sense to refer to a chloro, bromo, fluoro or iodo substituent. The terms "haloalkyl," "haloalkenyl" or "haloalkynyl" (or "halogenated alkyl," "halogenated alkenyl," or "halogenated alkynyl") refers to an alkyl, alkenyl or alkynyl group, respectively, in which at least one of the hydrogen atoms in the group has been replaced with a halogen atom.

The term "substituent" as used herein refers to a functional group or nonhydrogen substituent bound to an atom of a molecular moiety herein. Those skilled in the art will appreciate that the compounds and molecular segments drawn and defined herein may be unsubstituted, substituted as specifically indicated, or substituted with other substituents. Examples of substituents which may be present in the compounds of the invention include, but are not limited to, halo, particularly chloro; hydroxy; alkoxy, particularly lower alkoxy, such as methoxy, n-propoxy and t-butoxy; primary amino ($NH_2$); secondary amino, typically lower alkyl-substituted amino; tertiary amino, typically lower alkyl-disubstituted amino; nitro; acyloxy, which may be represented as R'COO—; acylamido, which may be represented as R'CONH— and thiol analogs thereof (R'CSO— and R'CSNH—, respectively), wherein R' is alkyl, typically lower alkyl; carboxy (—C(O)OH); alkoxycarbonyl (—C(O)OR'); carbamyl (—C(O)$NH_2$); alkylcarbamyl (C(O)NHR'); alkylsulfonyl (R'$SO_2$—); and alkylphosphonyl (R'P(OR')O—). The terms "alkyl," "alkenyl," "hydrocarbyl," etc. as used herein are intended to encompass not only unsubstituted groups but substituted groups containing one or more "substituents" as just defined.

"Optional" or "optionally" means that the subsequently described event or circumstance may or may not occur, and that the description includes instances where said event or circumstance occurs and instances where it does not. For example, the phrase "optionally present" selectable cleavage site means that the selectable cleavage site may or may not be present and that the description includes those instances where the selectable cleavage site is present as well as those instances where the selectable cleavage site is absent.

A novel strategy is disclosed and claimed herein for preparing oligomer segments of interest in purified form. Initially, the method involves preparing a support-bound oligomer containing the oligomer segment of interest to be provided in purified form. The support-bound oligomer is synthesized by sequentially coupling monomers to the terminus of a growing support-bound oligomer chain until the desired support-bound oligomer is obtained. The support-bound oligomer contains a first selectably cleavable linkage, a second selectably cleavable linkage, and a third selectably cleavable linkage, wherein the oligomer segment of interest is the segment flanked by the second and third selectably cleavable linkages, and wherein a first capture moiety is present at the free terminus of the support-bound oligomer, and a second capture moiety is present between the first and third selectably cleavable linkages. The selectably cleavable linkages and the capture moieties are introduced during synthesis using techniques described herein and/or known to those of ordinary skill in the art. The selectably cleavable linkages and the capture moieties are introduced during synthesis using techniques described herein and/or known to those of ordinary skill in the art. The support-bound oligomeric molecule used as the starting material in the purification process is shown schematically at the top of FIG. 1A and may be generally represented by formula (I)

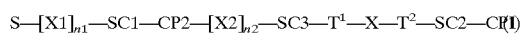

$$S—[X1]_{n1}—SC1—CP2—[X2]_{n2}—SC3—T^1—X—T^2—SC2—CP\ (I)$$

wherein S represents the solid support, X1 and X2 are monomers or oligomeric segments, n1 and n2 are independently zero or 1, SC1, SC2 and SC3 represent first, second and third selectably cleavable sites, CP1 and CP2 represent first and second capture moieties, $T^1$ is the first terminus of the oligomer segment of interest "X", and $T^2$ is the second terminus of the oligomer segment X.

Figure 1B:
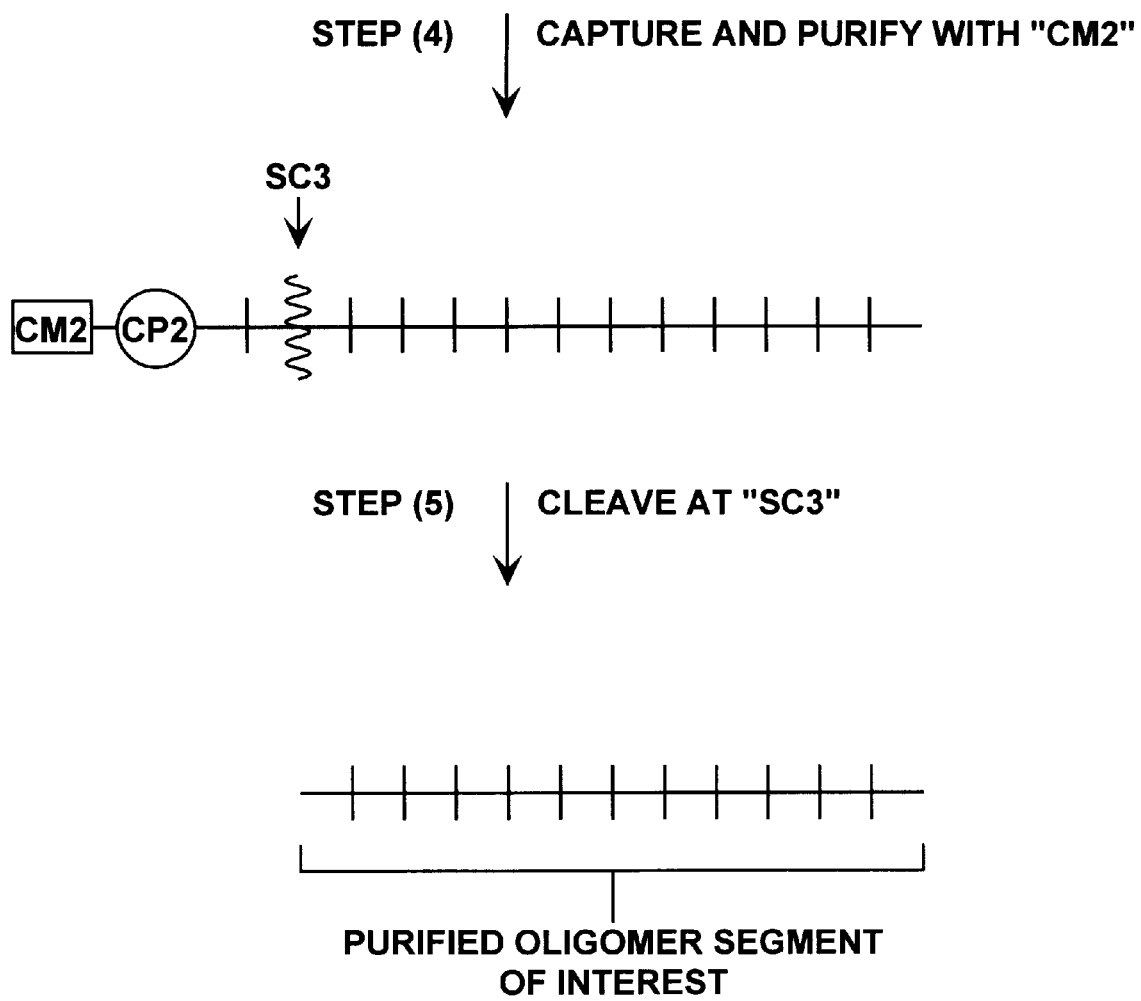

After synthesis of (I) is complete, a stepwise process is carried out in order to provide the oligomer segment of interest, $T^1$—X—$T^2$, in purified form. The steps of the process are illustrated schematically in FIGS. 1A and 1B. Initially, the first selectably cleavable linkage SC1 is cleaved so as to release the oligomeric product from the solid support (FIG. 1A, step 1). The released oligomeric product is then incubated with a first capture medium CM1 which couples to the first capture moiety CP1, and the "captured" oligomeric product is then isolated and optionally purified FIG. 1A, step 2). Next, the second selectably cleavable linkage SC2 is cleaved to produce the oligomer segment of interest terminating in a second capture moiety CP2 (FIG. 1A, step 3). The oligomer segment so provided is incubated with a second capture medium CM2 which couples to the second capture moiety CP2, and the captured oligomer segment is then isolated and optionally purified (FIG. 1B, step 4). Finally, the third selectably cleavable linkage (SC3) is cleaved to give the oligomer segment of interest in purified form.

For simplicity, the description which follows refers to oligomers comprised of oligonucleotides. However, it will be appreciated by those skilled in the art that the methodology can be readily adapted to prepare other types of purified oligomers using conventional techniques and reagents.

In one embodiment, then, a method is provided for preparing an oligonucleotide segment of interest in purified form using a support-bound oligonucleotide having the structure of formula (I) as a starting material. In this embodiment, $T^1$—X—$T^2$ represents the desired oligomer segment of interest, with $T^1$ and $T^2$ representing the 5' and 3' termini, respectively, of the oligonucleotide "X." Thus, with oligonucleotides, purification using the method of the invention employs both 3'- and 5'-selection techniques. 5'-Selection is based on the proven technique of DMT/RP chromatography. Horn et al. (1988) *Nucleic Acids Res.* 16:11559–71. However, 5'-selection alone is not adequate to isolate the product oligomer. The key step in the new strategy is 3' capture that selectively binds oligonucleotides with intact 3' termini, so that capture will only take place if the desired terminal moiety is present. Thus, randomly truncated oligonucleotides generated during deprotection will not be captured because they lack the 3' capture moiety. Capture results in the formation of a covalent linkage between oligomer and capture support, i.e., between CP1 and CM1 and between CP2 and CM2. After washing to remove oligomers that are not covalently bound, the captured oligomer is specifically released.

The scheme may be used in the purification of synthetic DNA oligomers, but can potentially be extended to other types of oligomers (RNA, PNA, peptoids, peptides, oligosaccharides and others). It is further possible to use any two capture techniques in the present purification schemes, for example, 5'-thiol and 3'-aldehyde capture, 3'-aldehyde and 5'-thiol capture, etc. One of skill in the art will recognize that an oligonucleotide can be synthesized either 5'→3' or 3'→5' and that the methods described herein, although exemplified using 3'→5' oligonucleotide synthesis, can be practiced using either synthetic scheme.

The invention enables purification of oligomers such that error-containing and incomplete oligomers are removed. This is achieved by employing 5' terminal blocking groups and capture moieties that provide means for separating complete, i.e., blocking group-containing and capture moiety-containing, oligomers and polymers. Separation may be effected using the blocking group-containing and capture moiety-containing oligomer as prepared or, optionally, the 5'-blocking group, the 3'-capture moiety or both may be modified to provide alternative means for purifying the oligomer.

5' CAPTURE AND THE 5' CAPTURE MOIETY:

Preferably, although not necessarily, the initial "capture" step in the purification scheme is a 5'-selection step. Typically, the 5' capture moiety, is dimethoxytrityl ("DMT"), monomethoxytrityl ("MMT"), trityl, pixyl, or the like, with DMT preferred. Other hydroxyl protecting groups include carbonate esters, such as 2-methylene-9,10,-anthraquinone carbonate ester and p-nitrobenzyl carbonate ester, as disclosed by Urdea et al., U.S. Pat. No. 5,703,218. The 9-fluorenyl-methylcarbonate ("Fmoc") group is also used for 5'-protection in solid-phase oligonucleotide synthesis (Fukuda et al. (1988) *Nucleic Acids Res. Synmposium Ser.* 19, 13, and C. Lehmann et al. (1989) *Nucleic Acids Res.* 17:2389). Similarly, R. L. Letsinger et al. (1967), *J. Am. Chem. Soc.* 32:296, describe using the p-nitrophenyloxycarbonyl group for 5'-hydroxyl protection. Hydrazine-labile 5' protecting groups include benzoylpropionyl groups (Letsinger el al. (1967) *J. Am. Chem. Soc.* 89:7147), and levulinyl ester groups (deRooij et al. (1979) *Real. Track. Chain. Pays-Bas.* 98:537, Iwai et al. (1988) *Tetrahedron Lett.* 29:5383; and Iwai et al. (1988) *Nucleic Acids Res.* 16:9443). The 5' selection step is effected by incubation with a capture medium such as a reverse phase chromatography medium, a hydrophobic interaction chromatography medium, or the like. In other words, a reverse-phase cartridge or bulk phase purification step can be used to select for oligomers containing the DMT moiety. Horn et al. (1988), supra.

5' Capture moieties that can be used to effect 5' capture using, e.g., reverse phase separation, hydrophobic interaction separation, or the like, include 2-(tritylthio)alkyl linkers having the formula 2-(tritylthio)-$R^1$—O—p—5'—O—$Nu^1$, wherein $R^1$ is lower alkyl, p is $P(O)_2$ and $Nu^1$ is a 5'-nucleotide. In this case, the 5'-terminal capture moiety is a trityl group and the 5'-cleavable linker is S—R'—O—p. Such derivatives, e.g., 2-(tritylthio)—$CH_2CH_2$—O—p—5'—O, are described in Connolly et al. (1985) *Nucleic Acids Res.* 13:4485–4502. Deprotection of the tritylthio group with $AgNO_3$ results in the generation of HS-alkyl-O—p—O-oligomer which spontaneously eliminates ethylene sulfide to yield a 5'-phosphorylated oligonucleotide. Accordingly, such a linker would be compatible with (i.e., orthogonally removable with respect to) a disilyloxy linker, which may be selectively cleaved with a fluoride reagent.

An additional 5' capture moiety that can be used to effect 5' capture by RP separation, hydrophobic interaction separation, or the like, and serves as a cleavable linker as well is $(\phi)_3Si$—$R^2$—O—p—5'—O—$Nu^1$, wherein $\phi$ is phenyl, $R^2$ is lower alkyl and $Nu^1$ is as defined above. Treatment with fluoride reagents such as tetrabutylammonium fluoride ("TBAF") and triethylamine trihydrofluoride ("TEA(HF)$_3$") results in fragmentation of the $(\phi)_3Si$—$R^2$—O—p—5'—O-oligomer into $(\phi)_3Si$—F, ethylene oxide, and 5'—p—O-oligomer. Such a linker moiety is incompatible with a disilyloxy linker, which is also cleaved using fluoride reagents. Examples of linkers such as $(\phi)_3Si$—$CH_2CH_2$—O—p—5'—O—Nu, are described in Celebuski et al. (1992) *J. Org. Chem.* 57:5535–5538, and in U.S. Pat. No. 5,380,835 to Celebuski et al., issued Jan. 10, 1995.

5'-Selection of such oligomers is conducted using capture schemes specific for the 5' capture moiety, thereby forming a covalent linkage with the first capture medium or capture support. In this case, it is necessary that a 5' cleavable linker be incorporated between the 5' capture moiety and the 5' terminus of the oligomer. In addition, it is preferred that the 5' cleavable linker is compatible with the 3' terminal linker.

Thus, for example, 5'-thiol capture may be effected to yield an oligomer bearing a 5'-terminal phosphate when the 5' capture moiety is DMT—O—$R^3$—S—S—$R^4$—O—p, in which $R^3$ and $R^4$ are independently lower alkylene, arylene, aralkylene, or alkarylene, and the 5' linker is "reverse L1" (i.e., orthogonal with respect to L1 linkers), which may be incorporated using as the last condensation monomer $N^4$—(DMT—O—$R^5$)-2',3'—O-benzoyl-ribocytidine 5'-(β-cyanoethyl)phosphoramidite, in which $R^5$ is lower alkylene, arylene, aralkylene, or alkarylene. Alternatively, $N^4$—(DMT—O—$R^5$)-2',3'—O-benzoyl-cytidine 5'-(β-cyanoethyl)phosphoramidite or $N^4$—(DMT—O—$R^5$)-5-methyl-2',3'—O-benzoyl-cytidine 5'-(β-cyanoethyl)

phosphoramidite may be incorporated as the last condensation monomer. Those of skill in the art will recognize that similarly derivatized guanosine, adenosine or uridine derivatives, e.g., $N^4$—(DMT—O—$R^5$)-2'3'—O-benzoyl-guanosine, $N^4$—(DMT—O—$R^5$)-2'3'—O-benzoyl-adenosine, and $N^4$—(DMT—O—$R^5$)-2'3'—O-benzoyl-uridine, or even abasic sites such as 1—O—(DMT—O—$R^5$)-2,3—O-dibenzoyl-ribose 5'-(β-cyanoethyl)phosphoramidite or 5—O—DMT-2,3-dibenzoyl-ribose 1—O-(β-cyanoethyl-O—$R^5$) may be incorporated as the last condensation monomer.

In one preferred embodiment, the 5' linker is "reverse L1" and $R^3$, $R^4$ and $R^5$ are —$C_6H_{12}$—. Reduction of the —S—S— bond using a reducing agent such as dithiothreitol ("DTT") yields an active thiol group by which capture may be effected as described below. 5'-thiol capture may be effected to yield a 5'-hydroxyl moiety wherein the 5' linker is —O—$R^6$—O—Si($R^7$)($R^8$)—O—Si($R^9$)($R^{10}$)-5'—O, wherein $R^6$, $R^7$, $R^8$, $R^9$, $R^{10}$ are independently lower alkyl, aryl, aralkyl, or alkaryl. Preferably, the 5' linker is —O—($CH_2$)$_3$—O—Si(CH($CH_3$)$_2$)$_2$—O—Si(CH($CH_3$)$_2$)$_2$-5'—O. Similarly, 5-dialdehyde capture may be effected in which the 5' capture moiety is 2',3'—O-(benzoyl)$_2$-riboNu-5'—p, wherein riboNu is a ribonucleotide and is preferably riboU, and the 5' linker is —O—$R^6$—O—Si($R^7$)($R^8$)—O—Si($R^9$)($R^{10}$)-5'—O, preferably —O—($CH_2$)$_3$—O—Si(CH($CH_3$)$_2$)$_2$—O—Si(CH($CH_3$)$_2$)$_2$-5'—O.

Alternatively, the 5' linkage may be a selectably cleavable abasic site as disclosed in U.S. Pat. No. 5,430,136. For example, an oligonucleotide chain may contain the structure

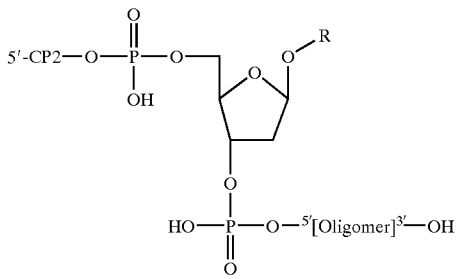

in which CP2 is a 5' capture moiety as defined above, "Oligomer" is a segment of the oligonucleotide, and R is selected from the group consisting of 2-nitrobenzyl, 4-penten-1-yl, —$CH_2CH_2$Sφ, —$CH_2CH_2Si(CH_3)_3$, —P(O)$O^-_2$, —$CH_2CH_2$—$C_6H_4$—$NO_2$, and 2-methylene-9,10-anthraquinone ("MAQ") moiety

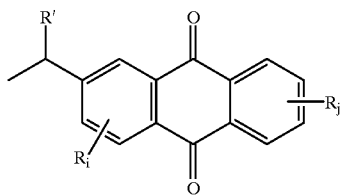

in which R' is hydrogen, aryl, or aralkyl, if aryl or aralkyl, preferably $C_1$–$C_8$ aryl or aralkyl, the $R_i$ may be the same or different and are selected from the group consisting of amino, nitro, halogeno, hydroxyl, lower alkyl and lower alkoxy, the $R_j$ may be the same or different and are selected from the group consisting of amino, nitro, halogeno, hydroxyl, lower alkyl and lower alkoxy, i is zero, 1, 2 or 3, and j is zero, 1, 2, 3 or 4. Cleavage of an oligonucleotide containing such an abasic site may be carried out as described in the '136 patent. That is, when R is 2-nitrobenzyl, cleavage may be effected via photolysis using UV light having a wavelength of at least 350 nm, followed by basic hydrolysis with, e.g., ammonium hydroxide or the like. When R is —$CH_2CH_2$Sφ (in which φ represents phenyl), cleavage is effected by oxidation of the sulfur atom to —SO— or —$SO_2$— with, e.g., sodium periodate, followed by treatment with base. When R is —$CH_2CH_2Si(CH_3)_3$, the oligonucleotide may be cleaved by treatment with, for example, fluoride ions, again followed by base. When R is MAQ, cleavage may be carried out by oxidation with $Na_2S_2O_4$, followed by treatment with base. When R is —$CH_2CH_2$—$C_6H_4$—$NO_2$, cleavage may be effected using 1,8-diazabicyclo[5.4.0 undec-7-ene]. When R is phosphate, removal may be effected with alkaline phosphatase followed by treatment with base, while when R is 4-penten-1-yl, cleavage will be carried out typically using N-bromosuccinimide, followed by treatment with base.

Other selectably cleavable linkages useful in conjunction with the present invention include, for example, enzyme-cleavable sites, e.g., linkages cleavable with restriction endonucleases, as described in U.S. Pat. No. 4,775,619 to Urdea et al., and pyrophosphate diester linkages, cleavable by pyrophosphatases. Additional selectably cleavable linkages are chemically cleavable sites, including, but not limited to: disulfide linkages, cleavable by reduction such as with Ellman's reagent or the like; 1,2-diols, cleavable by periodate; and other periodate-cleavable linkages such as —(CO)—CH(OH)—, —CH(NHR)—CH(OH)—, —(CO)—(CO)— and —CH(NHR)—CH(NHR)— wherein R is H or lower alkyl.

Preferably, the 5' capture moiety is different from the 3' capture moiety, e.g, a 5' thiol capture moiety or a 5' dialdehyde capture moiety is used with an oligomer bearing a 3' dialdehyde capture moiety or a 3' thiol capture moiety, respectively. In addition, as noted above, it is preferred that, when present, the 5' cleavable linker is compatible with, i.e., is not cleaved by the same treatment as, the 3' cleavable linker or, when both are present on the oligomer, the synthesis release moiety.

SOLID SUPPORT:

A wide variety of supports can be used for solid phase synthesis of an oligonucleotide. Examples of suitable support materials include, but are not limited to, polysaccharides such as agarose (e.g., that available commercially as Sepharose®, from Pharmacia) and dextran (e.g., those available commercially under the tradenames Sephadex®, Sephadex LH-20 and Sephacyl®, also from Pharmacia), polyacrylamides, poly(dimethylacrylamide), poly (acrylmorpholide), polystyrenes, polystyrene grafted onto poly(tetrafluoroethylene), polyvinyl alcohols, copolymers of hydroxyethyl methacrylate and methyl methacrylate, silicas, teflons, glasses, Porasil C, controlled pore glass ("CPG"), kieselguhr, cellulose, Fractosil 500, and the like, as described in U.S. Pat. No. 5,256,549 to Urdea et al., and references provided therein.

CLEAVABLE LINKERS CONNECTING THE OLIGOMER TO THE 3'-CAPTURE MOIETY:

Cleavable linkers used to connect the oligomer to the 3' capture moiety during synthesis and purification must be stable to the conditions of synthesis, selective cleavage from the solid support, deprotection, reverse phase/desalting/hydrophobic interaction chromatography, and covalent capture. Cleavage of this cleavable linker yields the final, purified oligomer with either a 3' phosphate or a free 3' hydroxyl group, depending on the linker used.

Selectably cleavable linkers used to connect the oligomer to the capture moiety and produce an oligomer having a 3' phosphate include $N^4$-(phosphoryl-6-oxyhexyl)cytidine ("L1") and 2',3'-isopropylidine-$N^4$-(phosphoryl-6-oxyhexyl)cytidine ("L2"). L1 may be cleaved, for example, using β-elimination after periodate oxidation of the 2',3'-diol system as described in Keith et al (1974) *Biochemistry* 13:3601–3606. L2 may be cleaved using acid to cleave the isopropylidine group, periodate oxidation of the 2',3'-diol system and β-elimination under basic conditions after periodate oxidation of the 2',3'-diol system. Keith et al., supra. Other cleavable linkers that may be used to connect the oligomer with the 3' capture moiety, or means by which to cleave the oligomer from the 3' capture to yield a 3'-phosphate include —P—O-alkylene$_1$-S-alkylene$_2$-O—p—, in which at least one of alkylene, and alkylene$_2$ is ethylene, and wherein elimination is effected after oxidation of —S— to —SO— (with periodate or N-chlorosuccinimide ("NCS") followed by treatment with base (Kamaike et al. (1993) *Nucleosides & Nucleolides* 12:1015–1032), acid cleavage of phosphoramidate linkage, $R^{11}$—O—p—NH—$R^{12}$ (Gryaznov et al. (1993) *Tetrahedron Lett.* 34:1261–1264), wherein $R^{11}$ is a nucleoside and $R^{12}$ is alkyl, aryl, aralkyl or alkaryl, allyl phosphate linkers that can be cleaved with palladium catalysis (Zhang et al. (1997) *Nucleic Acids Research* 25:3980–3983), and other linkers and cleaving means which are well known in the art.

Selectably cleavable linkers used to connect the oligomer to the capture moiety and produce an oligomer having a 3' hydroxyl group include linkers having the structural formula —$Nu^2$—3'—O—Si($R^{13}$)($R^{14}$)—O—Si($R^{15}$)($R^{16}$)—O—$R^{17}$, wherein $Nu^2$ is the terminal 3' nucleotide of the oligomer, $R^{13}$, $R^{14}$, $R^{15}$ and $R^{16}$ are independently lower alkyl, aryl, aralkyl, or alkaryl and $R^{17}$ is a capture moiety as disclosed herein, e.g., 1,1,3,3-tetraalkyl-disilyloxy as described in Kwiatkowski et al. (1996) *Nucleic Acids Research* 24:4632–4638. The disilyloxy linker may be cleaved using fluoride reagents such as TBAF and TEA (HF)$_3$ as described in Westman et al. (1994) Nucleic Acids Research 22:2430–2431. Other cleavable linkers that may be used to connect the oligomer with the 3' capture moiety which, upon cleavage, yield a 3'-phosphate include —$Nu^2$—O—Si($R^{18}$)($R^{19}$)-2—O—$R^{20}$ (Walsh et al. (1997) *Tetrahedron Letters* 38:651–1654), wherein $Nu^2$ is as defined above, $R^{18}$ and $R^{19}$ are independently lower alkyl, aryl, aralkyl, or alkaryl and $R^{20}$ is a capture moiety as disclosed herein and $Nu^2$—O—Si($R^{21}$)($R^{22}$)—$R^{23}$—Si($R^{24}$)($R^{25}$)—O—$R^{26}$, wherein $Nu^2$ is as defined herein, $R^{21}$, $R^{22}$, $R^{23}$, $R^{24}$ and $R^{25}$ are independently lower alkyl, aryl, aralkyl, or alkaryl and $R^{26}$ is a capture moiety as disclosed herein, e.g., $Nu^2$—O—Si(CH$_3$)$_2$—(CH$_2$)$_2$—Si(CH$_3$)$_2$—O—$R^{26}$, each of which is cleavable with fluoride reagents; and 2'—O—PG-ribonucleotide, in which the protecting group and the treatment for removal are selected from the group consisting of t-butyl-dimethyl-silyl (treatment with fluoride and then base), phosphate (alkaline phosphatase, base), 1-methoxycyclohexyl ether (0.01 M HCl, base; Reese et al. (1967) *J. Am. Chem. Soc.* 89:3366), methylthiomethyl ether (AgNO$_3$, base; Corey et al. (1975) *Tetrahedron Letters* 1975:3269–3270) and siloxymethyl ether (fluoride, base; Gundersen et al. (1989) *Acta Chem. Scand.* 43:706). After removal of 2'—O—PG group, the oligomer is cleaved from the riboside by treatment with strong base (leaving a cyclic phosphate) (Crea et al. (1980) *Nucleic Acids Res.* 8:2331–48; Schwartz et al. (1995) *Tetrahedron Letters* 36:27–30.); linkers having the formula, e.g., $Nu^2$—O—$R^{27}$S—$R^{28}$, wherein N is defined as above, $R^{27}$ is lower alkyl, aryl, aralkyl, or alkaryl, and $R^{28}$ is a capture moiety, e.g., thioformacetal derivatives such as $Nu^2$—O—CH$_2$S—$R^{28}$, which derivatives are cleavable with silver nitrate as described in Keck et al. (1978) J. Org. Chem. 31: 1031; linkers having the formula, $Nu^2$—O—$R^{29}$—O—$R^{30}$(NO$_2$), wherein Nu is as defined above and $R^{29}$ is lower alkyl and $R^{30}$ is aryl, aralkyl, or alkaryl, for example, 4-nitrobenzyloxymethyl derivatives such as $Nu^2$—O—CH$_2$—O—C$_6$H$_3$(NO$_2$), which derivatives are cleavable with fluoride as described in Gough et al. (1996) Tetrahedron Letters 37:981–982, and 2-nitrobenzyloxymethyl derivatives such as $Nu^2$—O—CH$_2$—O—C$_6$H$_3$(NO$_2$), and which derivatives are cleavable with photolysis as described in Pillai (1980) Synthesis 1980: 1–26; linkers derived from alkyldiolamines, e.g., 2,3-propanediolamine (HO—CH$_2$—CHOH—CH$_2$—NH$_2$), wherein the derivative has the formula $Nu^2$—O—p—O—$R^{31}$—NH(allyloxycarbonyl)O—, wherein Nu is as defined above and $R^{31}$ is lower alkyl, for example, $Nu^2$—O—p—O—CH$_2$—CH—CH$_2$—NH(allyloxycarbonyl)—O— as described in Lyttle et al. (1996) *Nucleic Acids Research* 24:2793–2798.

Alternatively, 3'-cleavable linkers may be selectably cleavable abasic sites having the formula

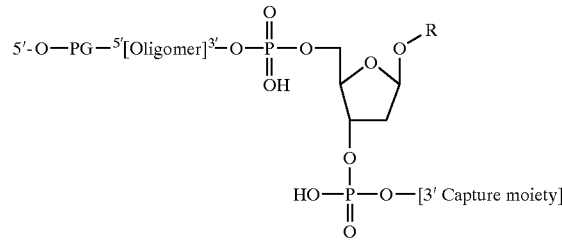

wherein PG may be DMT or the like, and R is as defined previously. Still other linkages suitable as the 3' linker are those described above as useful at the 5' site; however, as emphasized herein, the 3' and 5' linkers should be orthogonally cleavable with respect to each other.

3' CAPTURE SCHEMES:

A variety of 3'-capture schemes are used to purify an oligomer in combination with a 5' capture scheme. Examples of such 3'-capture schemes include, but are not limited to, the following: thiol capture schemes using a capture medium selected from the group consisting of solid support-S—S-pyridine, bromoacetyl-solid support, solid support-NH—CO—NH-phenyl-NCS and solid support-epoxy in which the oligomer is released from the solid support and bears a thiol group; a "reverse" thiol capture scheme in which the released oligomer contains a 3'-bromoacetyl- or malimido moiety and the oligomer is captured on a support bearing a thiol moiety; capture of a oligomer which, on release from the solid support, bears an aldehyde moiety and capture is effected using a solid support-CO—NRNH$_2$ (Timofeev et al. (1996) *Nucleic Acids Research* 24:3142–3148; Hansske et al. (1974) *Bioorganic Chemistry* 3:367–376); a "reverse" aldehyde capture scheme in which the oligomer is released from the solid support and bearing a hydrazide group and in which capture is effected on an aldehyde support; (6-histaminylpurine)$_6$ (His$_6$) capture using nickel-nitrilotriacetic acid ("Ni—NTA") by immobilized metal affinity chromatography, i.e., CPG—Ni—NTA as described in Orum et al. (1995) *BioTechniques* 19:472–480; Minet al. (1996) *Nucleic Acids Research* 24:3806–3810; amine capture on CPG-DITC (CPG-phenyl-NCS) (Urdea et al. (1988) *Nucleic Acids Res.* 16:4937–56) or CPG-epoxy; diol capture on boric acid support (Mazzeo (1989) *BioTechniques* 4: 124–130; Pace et al. (1980) *Analytical Biochemistry* 107:128–135); biotin capture on avidin support or avidin capture on biotin support; dinitrophenyl capture on anti-DNP support (Grzybowski et al. (1993) *Nucleic Acids Research* 21:1705–1712); and Diels-Alder capture as described in Wang et al. (1997) *Chem. Commun.* 1997:1495–1496. Of the above listed 3' capture schemes, thiol capture and aldehyde capture are preferred.

Thiol capture—In this capture scheme, the oligomer is synthesized on a support that contains a disulfide linkage 5'—DMT-Oligo-3'—p—O-alkylene-S—S-alkylene-O-succinyl-CPG, e.g., 5'—DMT-Oligo-3'—p—O—$(CH_2)_3$—S—S—$(CH_2)_3$—O-succinyl-CPG. After standard ammonium hydroxide deprotection, the oligomer is present as 5'—DMT-Oligo-3'—p—O—$(CH_2)_3$—S—S—$(CH_2)_3$—OH. Subsequent treatment with a reducing agent, for example, tris (2-carboxyethyl)phosphine hydrochloride ("TCEP") or dithiothreitol ("DTT"), cleaves the disulfide bridge to give 5'—DMT-Oligo-3'—p—O—$(CH_2)_3$—SH. The preparation of 5'-thiolated oligodeoxynucleotides has been described (Kumar et al. (1996) *Bioorg. Med. Chem. Lett.* 6:683–688; Bischoff et al. (1987) *Analytical Biochemistry* 164:336–344; Kuijpers et al. (1993) *Tetrahedron* 49:10931–44). The solid-phase synthesis of 3'-thiol oligomers using 3'-sulfhydryl supports can accomplished by techniques well known in the art; see, e.g., Gupta et al. (1991) *Nucleic Acids Research* 19:3019–3025.

Purification of an oligomer according to this scheme involves a three-step process. The oligomer released from the solid support is subject to purification using 5' capture and a Baker Phenyl column (BP) or other means to remove excess reducing agent and some non-DMT species. All DMT-containing species may be eluted, for example, with a solution of 75% methanol containing 50 mM TEAA.

Alternatively, the DMT-containing species can be separated from excess reducing agent using a desalting column, a hydrophobic interaction column or other separation means that selects on the basis of size (e.g., for desalting) or hydrophobicity, e.g., to separate DMT-containing species from DMT-lacking species.

The eluant containing the DMT-containing species is then subject to capture on an activated thiol capture support, e.g., CPG—S—S-pyridine. This may be accomplished by applying the eluant to a short column of activated thiol capture support, CPG—S—S-pyridine. Alternatively, the separation may be done using a batch separation protocol. Unbound material is washed away with high salt buffer, e.g., 0.5 M NaCl in 10 mM Tris, pH 8.

The captured oligomer is then recovered by either (1) releasing the oligomer into solution from the capture support sequence using a reducing agent, e.g., DTT, and then cleaving the 3' cleavable linker in solution, e.g., for the disilyloxy linker, or (2) oxidation of the linker molecule in the captured oligomers with sodium periodate, e.g, for the L1 linker followed by treatment with mild base in a high salt buffer.

Further purification of the oligomer may be effected by applying the product of the foregoing 3' capture step to a reverse phase or hydrophobic interaction column to take advantage of the presence of the 5'—O—DMT as described in Horn et al. (1988), supra.

An example of oligonucleotide purification by combined thiol capture/DMT selection using an L1 3' cleavable linker is illustrated in Scheme 1. Scheme 1A illustrates an oligonucleotide product ($T_3dAT_3$) that has been released from the solid support and comprises a 5'—O—DMT group and a 3'—CM1—p—$(CH_2)_3$—S—S—$(CH_2)_3$—OH moiety. In addition to the desired oligonucleotide species (1) the product is contaminated with an oligonucleotide that contains an abasic site (2). The abasic site can result from deprotection of exocyclic amines and phosphate groups in the oligomer prior to release from the solid support. Ammonium hydroxide deprotection treatment of the full-length oligomer results in at least the three species shown in Scheme 1B: (a) the fully deprotected intact full-length oligomer bearing a 5'—O—DMT moiety and a 3'—CM1—p—$(CH_2)_3$—S—S—$(CH_2)_3$—OH moiety (1); (2) a species having a 5'—O—DMT moiety and a 3' terminus having an apurinic moiety (3); and (3) a species having a 5' phosphate and a 3'—CM1—p—$(CH_2)_3$—S—S—$(CH_2)_3$—OH moiety (4). Treatment of the deprotected species with a reducing agent, e.g., DTT, results in conversion of the 3'—CM1—p—$(CH_2)_3$—S—S—$(CH_2)_3$—OH in species (1) and (4) to 3'—CM1—p—$(CH_2)_3$—SH (Scheme 1C).

Passage of a solution comprising species (1), (3) and (4) over a BP reverse-phase column results in retention thereon of species (1) and (3), which have a 5'—O—DMT moiety. Species (4) would not be retained (Scheme 1D). As illustrated in Schemes 1D–1E, exposure of species (1) and (3) to an activated thiol capture support, e.g., CPG—S—S-pyridine, results in covalent capture of only species (1) to form species (5), thereby effecting purification of a full-length oligomer by 5' and 3' selection. Scheme 1E illustrates release of the purified oligomer from the capture support by periodate oxidative cleavage of the ribo-diol system to form species (6) and beta-elimination under basic conditions to result in release full-length purified $T_3dAT_3$-3'—p (7). In Scheme 1E, only the 3' portion of species (6) and (7) are shown. An additional reverse phase column purification step may be performed prior to detritylation of the oligomer.

Scheme 2 provides an example of a 3'-thiol capture process similar to that illustrated in Scheme 1, wherein the 3' moiety is —Nu-3'—O—Si(alkyl)$_2$—O—Si(alkyl)$_2$—p—(alkyl)—S—S—(alkyl)—OH, e.g., —Nu-3'—O—Si(CH(CH$_3$)CH$_2$)$_2$—O—Si(CH(CH$_3$)CH$_2$)$_2$—p—$(CH_2)_3$—S—S—Pr—OH. Purification is likewise similar to that described with respect to Scheme 1. However, the captured oligonucleotide is released with DTT from the support followed by cleavage of the disilyloxy linker using a fluoride reagent, e.g., such as TBAF and TEA(HF)$_3$.

SCHEME 1A
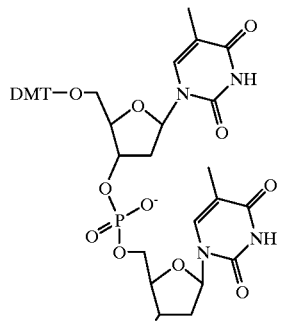 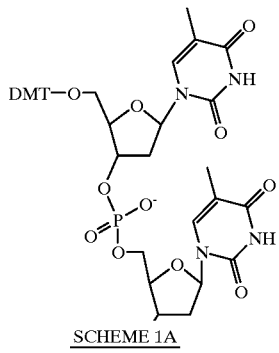
SCHEME 1A
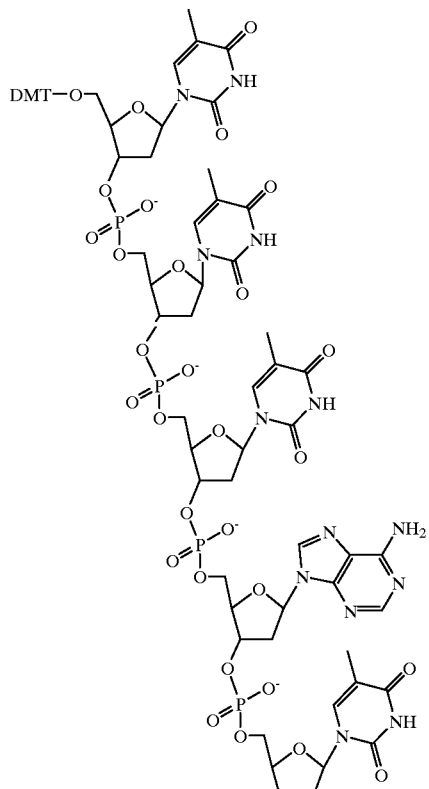 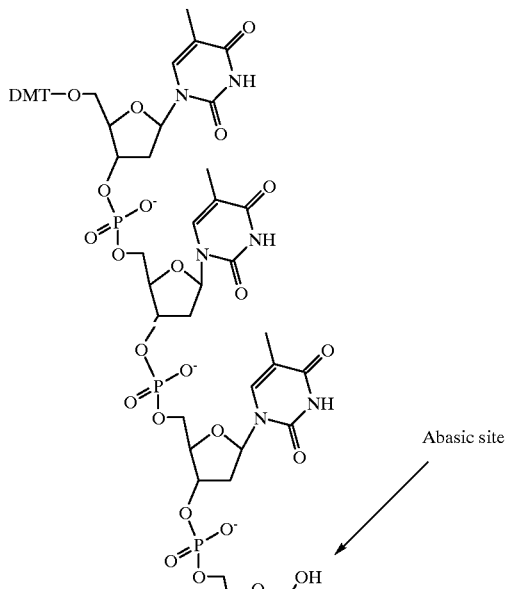
Abasic site
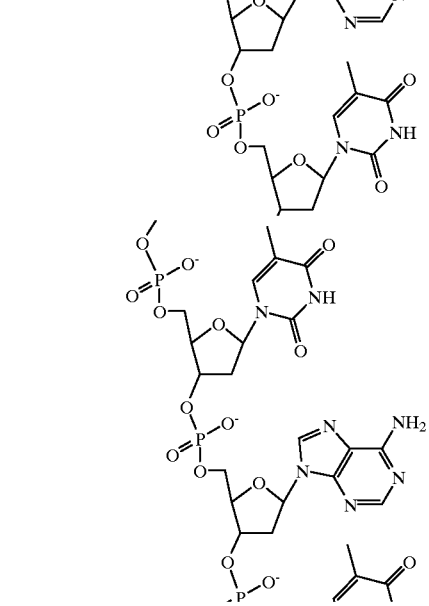 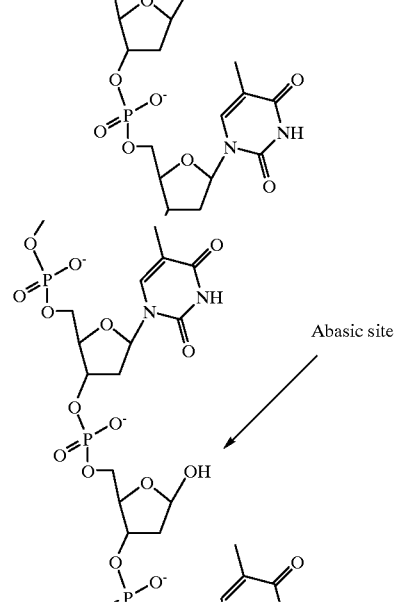
Abasic site Aldehyde capture—The oligomer is synthesized on a standard ribonucleoside solid support and released. Treatment of the terminal ribonucleoside at the 3' end of the oligomer with sodium periodate will generate a reactive nucleoside intermediate with two adjacent aldehyde groups; these can react in concert with hydrazido groups on the support to form stable morpholino intermediates. Purification using aldehyde capture is effected using the following steps.

The 5'—DMT-oligomer-3'—p—ribonucleotide is oxidized with sodium periodate to yield a 5'—DMT-oligomer-3'—p—ribonucleotide$_{(ox)}$ with two aldehyde groups. See, e.g., Hansske et al. (1974), supra. The oxidized construct is captured on a solid support having a pendant hydrazido groups, e.g., solid support-CO—NHNH$_2$, thereby forming stable morpholino intermediates. Unbound material is washed away with high salt buffer as described in Hansske et al. (1974), supra. The 3'-captured sequence is released by cleavage of the linker moiety while the oligomer is attached to the support for orthogonal linkers, e.g., the disilyloxy and L2 linkers. However, the L1 linker would not be considered an orthogonal linker in this situation because oxidation of the ribonucleotide capture moiety would also result in oxidation of the L1 ribo-diol system contained therein. Optionally, the solution with released material is directly applied to a Baker Phenyl cartridge as described in Horn et al. (1988), supra.

An example of oligonucleotide purification by combined aldehyde capture/DMT selection using an abasic site 3' cleavable linker is illustrated in Scheme 3. Scheme 3A illustrates the preparation of an oligonucleotide product that has been released from the solid support and comprises a 5'—O—DMT group and a 3'-abasic site-p-ribocytidine moiety. Furthermore, the oligonucleotide contains a second abasic site which, as described above, is illustrative of a result from deprotection of exocyclic amines and phosphate groups in the oligomer prior to release from the solid support. Ammonium hydroxide deprotection treatment of the full-length oligomer results in at least the three species shown in Scheme 3B: (1) the fully deprotected intact full-length oligomer bearing a 5'—O—DMT moiety and a 3'-abasic site-p-ribocytidine moiety (1); (2) a species having a 5'—O—DMT moiety and a 3'—OH (3); and (3) a species having a 5' phosphate and a 3'-abasic site-p-ribocytidine moiety (4).

Passage of a solution comprising species (1), (3) and (4) over a BP column would result in retention thereon of species (1) and (3), which have a 5'—O—DMT moiety. The third species would not be retained. Periodate oxidation of the ribo-diol system of the ribocytidine moiety of species (1) and (3) results in the generation of a dialdehyde moiety in species (1'). As illustrated in Scheme 3C, exposure of species (1') and (3) to an support-bound hydrazide, e.g., CPG-hydrazide, results in capture of only species (1'), thereby effecting purification of a full-length oligomer by 5' and 3' selection. Scheme 3D illustrates release of the purified oligomer from the capture support by cleavage of the abasic site. An additional reverse phase column purification step may be performed prior to detritylation of the oligomer.

SCHEME 3A

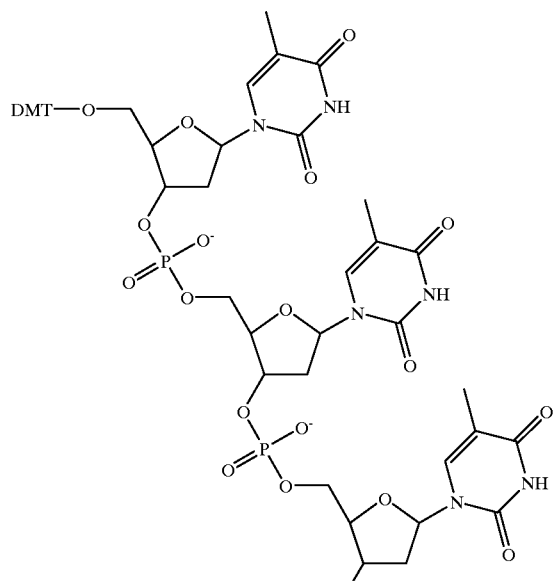

-continued
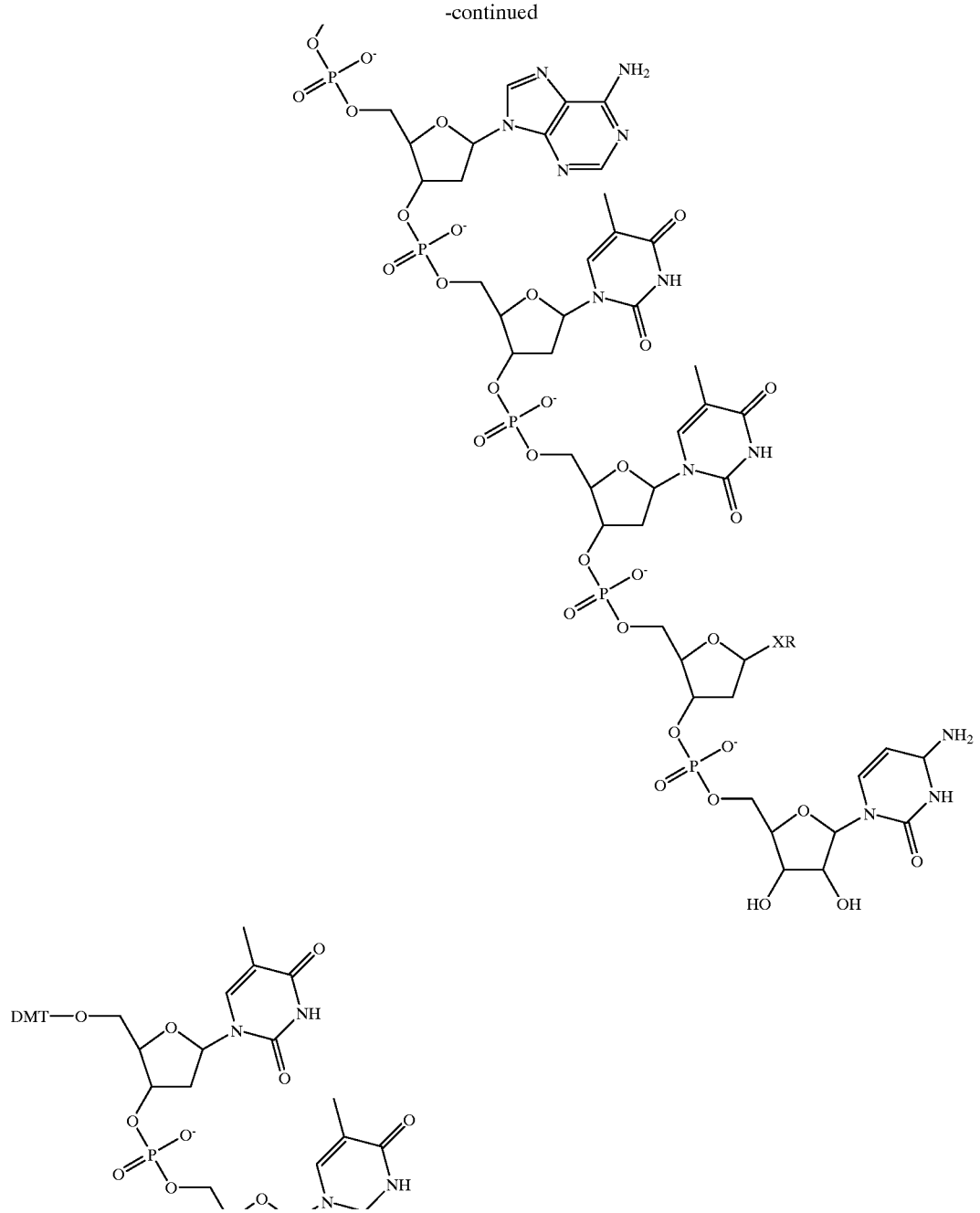

Additional Schemes for Purifying Oligonucleotides—
Additional 3' capture schemes include $His_6$ capture using Ni—NTA by immobilized metal affinity chromatography, i.e., CPG—Ni—NTA (see Scheme 4), amine capture using immobilized moieties that react with primary amines, e.g., DITC or phenyl-NCS, ribonucleotide capture using immobilized boric acid, capture on a boric acid column, 3'-biotinylated oligomer capture on an avidin-derivatized solid support, 3'-dintrophenylated oligomer capture on anti-dinitrophenol antibody-bearing solid support, and the like.

PURIFICATION OF PEPTIDES, PEPTOIDS AND PNAS:

N-Terminus—A special linker for the N-terminus of peptides, peptoids and PNAs that can be used in connection with a suitable purification moiety such as described in Canne et al. (1997) *Tetrahedron Letters* 38:3361–3364. The special derivatized aminoethylsulfonylethyloxycarbonyl handle is cleaved with base. It is stable to strong acid, including HF.

In a preferred embodiment, aminoethylthioethyloxycarbonyl ("AETEOC"; $NH-(CH_2)_2-S-(CH_2)_2-O-CO-$,) is used to connect a biopolymer to a suitable capture moiety as described above. AETEOC is more stable to basic conditions than its sulfonyl counterpart. Upon treatment with periodate, AETEOC is oxidized to aminoethylsulfoethyloxycarbonyl ($-NH-(CH_2)_2-SO-(CH_2)_2-O-CO-$) which is stable to strong acid, including HF, and can be cleaved with base.

C-terminus—Peptides, peptoids and PNAs can be prepared such that the C-terminus harbors a capture moiety, such as carboxyhydrazide moiety, an —S—S— linkage, a cysteine residue, or the like, by methods well known in the art. Such C-terminus capture moieties can be used to purify the biopolymer by methods disclosed herein and as exemplified below.

This invention outlines a simple two-cartridge purification method that dramatically reduces the hands-on time involved in routine purification of oligomers, in particular oligonucleotides, and delivers an oligomer having a purity of greater than 95% for a synthetic 30-mer oligonucleotide on a 1 micromole scale without the use of gels and HPLC. The simplified approach also lends itself to automation.

It is to be understood that while the invention has been described in conjunction with the preferred specific embodiments thereof, that the description above as well as the examples which follow are intended to illustrate and not limit the scope of the invention. Other aspects, advantages and modifications within the scope of the invention will be apparent to those skilled in the art to which the invention pertains.

All patents, patent applications, and publications mentioned herein, both supra and infra, are hereby incorporated by reference.

EXPERIMENTAL:

The practice of the present invention will employ, unless otherwise indicated, conventional techniques of synthetic organic chemistry, biochemistry, molecular biology, and the like, which are within the skill of the art. Such techniques are explained fully in the literature. See, e.g., Sambrook et al. (1989) *Molecular Cloning: A Laboratory Manual*, Second Edition (1989); *Oligonucleotide Synthesis* (M. J. Gait, ed., 1984); *Nucleic Acid Hybridization* (Hames et al., eds., 1984); and the series, *Methods in Enzymolgy* (Academic Press, Inc.).

In the following examples, efforts have been made to ensure accuracy with respect to numbers used (e.g., amounts, temperature, etc.) but some experimental error and deviation should be accounted for. Temperature is always given in degrees C. and, unless otherwise indicated, pressure is at or near atmospheric.

SOLID PHASE SYNTHESIS:

Polynucleotides may be assembled using a combination of solid phase direct oligonucleotide synthesis, enzymatic ligation methods, and solution phase chemical synthesis as described in detail in U.S. Pat. No. 5,710,264 to Urdea et al.

All chemical syntheses of oligonucleotides can be performed on an automatic DNA synthesizer (Perkin Elmer/Applied Biosystems Division model 380 B). Phosphoramidite chemistry of the β-cyanoethyl type was used including 5'-phosphorylation which employed PHOSTEL™ reagent ($DMT-O-CH_2CH_2-(SO_2)-CH_2CH_2-O-P(N(CH(CH_3)CH_2)_2)(-O-CH_2CH_2CN)$ wherein DMT is dimethoxytrityl is isopropyl). Standard manufacturer's protocols were used unless otherwise indicated.

PREPARATION OF CAPTURE SUPPORTS:

Preparation of $CPG-Pr-NH-CO-(CH_2)_2-S-S$-pyridine: $CPG-(CH_2)_3-NH_2$ was prepared as described in Horn (1997) *Nucleic Acids Research* 25:4835–4841. Two grams of $CPG-(CH_2)_3-NH_2$ was suspended in DMF containing 200 mg 3,3'-dithiodipropionic acid and 1,3-diisopropylcarbodiimide (1 ml), and the container was shaken on a mechanical shaker for 18 h. The CPG was transferred to a 100 ml funnel with a medium fritted filter and washed with 5×75 ml DMF, 5×75 ml methanol, and air dried. The support, $CPG-(CH_2)_3-NH-CO-(CH_2)_2-S-S-(CH_2)_2-COOH$, tested negative for amines (Ninhydrin).

$CPG-(CH_2)_3-NH-CO-(CH_2)_2-S-S-(CH_2)_2-COOH$ was treated with 20 ml of 0.1 M DTT in Maxim-Gilbert buffer, and the container was shaken on a mechanical shaker for 2 hours to reduce all disulfide bridges. The CPG was washed extensively with 5×75 ml Maxim-Gilbert buffer, 5×75 ml water, 5×75 ml methanol, and air dried. $CPG-(CH_2)_3-NH-CO-(CH_2)_2-SH$ tested strongly positive for thiols with Ellman's reagent.

$CPG-(CH_2)_3-NH-CO-(CH_2)_2-SH$ was treated with 20 ml 0.2 M pyridine-S—S-pyridine in DMF and the container was shaken on a mechanical shaker for 2 hours. The CPG was washed extensively with 5×75 ml DMF, 5×75 ml methanol, and air dried to give $CPG-(CH_2)_3-NH-CO-(CH_2)_2-S-S$-pyridine ("CPG—SSPy").

Alternatively, the capture support was prepared according to the method of Hermanson et al. (1992) *Immobilized Affinity Ligand Techniques* (Academic Press, San Diego, Calif.) pp. 274–279. Briefly, $CPG-(CH_2)_3NH_2$ (CPG Inc.; 5 grams) was suspended in 50 ml of 1 M $NaHCO_3$ containing 5 grams of N-acetyl homocysteine S-thiolactone, and the CPG was shaken for 24 hours at room temperature. The resulting support was washed extensively with 50 mM triethylammonium acetate, water, methanol, acetonitrile and air dried. The CPG—SH support contained 25 micromole/gram of free amine groups and 60 micromole/gram of sulfhydryl groups.

Activation of the CPG—SH was done by treating 3.5 grams of CPG—SH support with 30 ml of 0.2 M 2,2'-dipyridyl disulfide in N,N-dimethylformamide (DMF), and the mixture was left shaking for 24 hours at room temperature. The activated support was washed extensively with DMF, methanol, acetonitrile and air dried.

EXAMPLE 1

Preparation and Purification of an Oligomer with a Free 3'—OH

Oligomer Synthesis: The oligomer was synthesized on a special support, $DMT-T-Si_2-p-(CH_2)_3-SS-(CH_2)$ $_3$—O—Succ—NH—(CH$_2$)$_3$—CPG. At the conclusion of the synthesis, the final DMT was left on. Prior to removal of the oligomer from the support, the solid-supported oligomer was treated with 15% t-butylamine in acetonitrile to remove all β-cyanoethyl (BCE) phosphate protecting groups; this is done to avoid potential side-reaction of liberated acrylonitrile with sulfhydryl and amino groups through Michael addition (involving the double bond in acrylonitrile). The oligomer was then cleaved from the support and fully deprotected with ammonium hydroxide at 20° C. and 55° C. for 18 hours.

Purification: The fully deprotected oligomer was treated with a large excess of DTT in Maxim-Gilbert buffer for 1 hour. The DTT and Maxim-Gilbert buffer were removed using a reverse-phase cartridge, Baker Phenyl SPE column containing 500 mg phenyl-derivatized silica. Elution with 30% methanol in 50 mM triethylammonium acetate (30% MeOH/TEAA) resulted in incomplete elution of non-DMT oligomers; 75% MeOH/TEAA eluted all non-DMT and DMT oligomer species. The 75% MeOH/TEAA eluent was directly applied to the capture support, CPG—SSPy. The solution (10 ml) was allowed to percolate through the capture support (over 30 min); the capture was followed by UV which indicated that all UV material was retained on the capture support with concomitant release of Py—S— absorbing at 350 nm. The capture support was washed with 75% MeOH/TEAA (10 ml) and with Maxim-Gilbert buffer (10 ml), which was allowed to percolate through the capture support (over 30 min). The Maxim-Gilbert buffer wash was applied to a fresh BP and oligomeric material re-isolated. The Maxim-Gilbert buffer wash completely removed all oligomers that lacked the 3'-sulfhydryl capture functionality. Captured oligomeric material was released with DTT/ Maxim-Gilbert buffer (1 ml), which was allowed to percolate through the capture support (over 30 min). The DTT/ Maxim-Gilbert buffer solution containing the released oligomeric material was diluted with water (4 ml), and 1 ml of concentrated TEA(UF)$_3$ was added and the reaction allowed to go for 2 hours. The mixture was directly applied to an Oligonucleotide Purification Cartridge ("OPC") (ABI), and washed with TEAA. Elution with 30% MeOH/TEAA completely removed non-DMT oligomers, and 75% MeOH/ TEAA eluted the product oligomer in pure form. Evaporation and detritylation yielded the purified oligomer. Capture efficiency was determined to be about 65%.

EXAMPLE 2

Preparation and Purification of an Oligomer with a 3'-Phosphate

Oligonucleotide Synthesis: The oligomer was synthesized on a special support, DMT—L1—p—(CH$_2$)$_2$—SS—(CH$_2$)$_2$—O—Succ—NH—(CH$_2$)$_2$—CPG. At the conclusion of the synthesis the final DMT was left on. Prior to removal of the oligomer from the support the solid-supported oligomer was treated with 15% t-butylamine in acetonitrile to remove all BCE phosphate protecting groups; this was done to avoid potential side-reaction of liberated acrylonitrile with sulfhydryl and amino groups through Michael addition (involving the double bond in acrylonitrile). The oligomer was then cleaved from the support and fully deprotected with ammonium hydroxide at 20° C. and 55° C. for 18 hours.

Purification: The fully deprotected oligomer was treated with a large excess of DTT in Maxim-Gilbert buffer for 1 hour. The DTT and Maxim-Gilbert buffer were removed using a BP reverse-phase cartridge. Elution with 30% methanol in 50 mM triethylammonium acetate (30% MeOH/ TEAA) resulted in incomplete elution of non-DMT oligomers; 75% MeOH/TEAA eluted all non-DMT and DMT oligomer species. The 75% MeOH/TEAA eluent was directly applied to the capture support, CPG—SSPy. The solution (10 ml) was allowed to percolate through the capture support (over 30 min); the capture was followed by UV which indicated that all UV material was retained on the capture support with concomitant release of Py—S— absorbing at 350 nm. The capture support was washed with 75% MeOH/TEAA (10 ml) and with Maxim-Gilbert buffer (10 ml), which was allowed to percolate through the capture support (over 30 min). The Maxim-Gilbert buffer wash was applied to a fresh BP and oligomeric material re-isolated. The Maxim-Gilbert buffer wash completely removed all oligomers that lacked the 3'-sulfhydryl capture functionality. (Captured oligomeric material could be released with DTT/ Maxim-Gilbert buffer (1 ml), which was allowed to percolate through the capture support (over 10 min); the released oligomeric material could be recovered using a BP column.) The captured oligomeric material was released from the capture support in the 3'-phosphate form by a two-step procedure. Treatment with 1) sodium periodate solution resulted in the oxidation of the cis-diol system in CM1 of the solid-supported oligomeric material. Release from the capture support was achieved with 2) 20 mM NaOH/Maxim-Gilbert buffer. The mixture was directly applied to a BP cartridge and washed with TEAA. Elution with 30% MeOH/ TEAA completely removed non-DMT oligomers, and 75% MeOH/TEAA eluted the product oligomer in pure form. Evaporation and detritylation yielded the purified oligomer. Capture efficiency was determined to be about 65%.

In an alternative procedure, the crude deprotected oligomer was treated with DTT/MG to cleave the —S—S— linkage and excess reagent removed using a BP column. The solution containing the free 3'—X—SH was evaporated to dryness and dissolved in Maxim-Gilbert buffer (1 ml) and applied directly to a column of CPG—Pr—SSPy (CPG Inc.). Oligomer fragments which lacked the 3'-sulfhydryl group were removed by washing with TEAA containing methanol. The product oligomer was released and isolated as described above. Capture efficiency was about 33%.

EXAMPLE 3

Preparation and Purification of a Polypeptide Having A C-Terminus Carboxyhydrazide and an N-Terminus FMOC Polypeptide Synthesis: The oligomer is synthesized on a Wang-type support (H$_2$N—NH—CO—O—C(CH$_3$)$_2$—(CH$_2$)$_2$-φ-Polymer. Elongation of the polypeptide is accomplished using monomer units having the structure Fmoc-NH-aa(benzyl)—COOH, wherein "aa(benzyl)" is an amino acid having a benzyl side-chain protecting group. The final immobilized oligopeptide has the structure Fmoc-NH—[aa (benzyl)—CO]$_n$—NE-aa$_1$(benzyl)—CO—NH—NH—CO—O—C(CH$_3$)$_2$-(CH$_2$)$_2$-φ-polymer. Standard acid deprotection results in removal of benzyl side-chain groups and release of the oligopeptide in a partially protected form: Fmoc-NH-peptide-CO—NH—NH$_2$.

Purification: The partially protected oligopeptide is captured on a capture support bearing aldehyde moieties as described above to yield Fmoc-NH-peptide-CO—NH—N=CH-support. Release of the bound oligopeptide from the capture support in the same form as attached is achieved by cleaving CO—NH—N= via exchange with formaldehyde (Teitelbaum (1958) *J. Org. Chem.* 23 :646–647). Alternatively, the free acid form of the bound oligopeptide is released by direct oxidation and hydrolysis (Barton et al. (1972) *J. Chem. Soc., Perkins Trans. I* 1972:929).

Passing the partially protected oligopeptide released from the capture support over a hydrophobic chromatography column results in retention of the Fmoc-bearing species. The Fmoc group is then removed by treatment with base and the CO—NH—NH$_2$ is removed by oxidation and hydrolysis (Teitelbaum, supra) if it is not already in the carboxylate form.

EXAMPLE 4

Preparation Purification of a Polypeptide Having A C-Terminus Carboxyhydrazide and an N-Terminus Capture Moiety Polypeptide Synthesis: The oligomer is synthesized on a Wang-type support H$_2$N—NH—CO—O—C(CH$_3$)$_2$—(CH$_2$)$_2$—φ-Polymer. Elongation of the polypeptide is accomplished using monomer units having the structure Fmoc-NH-aa(benzyl)—COOH, as described in Example 3 above. The final immobilized oligopeptide has the structure Fmoc-NH-[aa(benzyl)—CO]$_n$—NH—aa$_1$(benzyl)—CO—NH—NH—CO—O—C(CH$_3$)$_2$—(CH$_2$)$_2$-φ-polymer. Additional synthetic procedures well known to those of skill in the art are used to add a special linker, if required, and a capture moiety ("CM") to yield CM—NH—(CH$_2$)$_2$—S—(CH$_2$)$_2$—O-Peptide-CO—NH—NE—CO—O—C(CH$_3$)$_2$—(CH$_2$)$_2$—φ-polymer. Standard acid deprotection results in removal of benzyl side-chain groups and release of the oligopeptide in a partially protected form: CM—NH—(CH$_2$)$_2$—S—(CH$_2$)$_2$—O-Peptide-CO—NH—NH$_2$.

Purification: The partially protected oligopeptide is captured on a capture support bearing aldehyde moieties as described above to yield CM—NH—(CH$_2$)$_2$—S—(CH$_2$)$_2$—O-Peptide-CO—NH—NH$_2$-support. Release of the bound oligopeptide from the capture support in the same form as attached is achieved by cleaving CO—Ni—N= via exchange with formaldehyde (Teitelbaum, supra). Alternatively, the free acid form of the bound oligopeptide is released by direct oxidation and hydrolysis (Barton et al., supra).

The partially protected oligopeptide bearing the Capture Moiety released from the capture support is captured using a support medium bearing a moiety with which the Capture Moiety can specifically interact, e.g., if the Capture Moiety is biotin, the solid support will bear an avidin moiety, if the Capture Moiety is His$_6$, the solid support will bear an Ni—NTA moiety, or the like. Release from the capture support to yield the purified oligopeptide is achieved by oxidation followed by treatment with base.

EXAMPLE 5

Preparation and Purification of a Polypeptide having A C-Terminus Sulfhydryl and an N-Terminus FMOC Polypeptide Synthesis: The oligomer is synthesized on a Wang-type support Fmoc-NH—CH(COOR)—CH$_2$—S—S—R—NH—CO—O—C(CH$_3$)$_2$—(CH$_2$)$_2$—φ-Polymer. Elongation of the polypeptide is accomplished using monomer units having the structure Fmoc-NH-aa(benzyl)—COOH, as described in Example 3 above, to yield Fmoc-NH-peptide-CO—NH—CH(COOR)—CH$_2$—S—S—R—NH—CO—O—C(CH$_3$)$_2$—(CH$_2$)$_2$—φ-Polymer. Deprotection of the bound polypeptide yields Fmoc-NH-peptide-CO—NH—CH(COOR)—CH$_2$—S—S—R—NH$_2$.

Treatment with a reducing agent such as dithiothreitol yields Fmoc-NE-peptide-CO—NH—CH(COOR)—CH$_2$—SH.

Purification: The partially protected oligopeptide is captured on a capture support—S—S—pyridine as described above to yield Fmoc-NH-peptide-CO—NH—CH(COOR)—CH$_2$—S—S-capture support. Release of the bound oligopeptide from the capture support is achieved by treatment with DTT to yield Fmoc-NH-peptide-CO—NH—CH(COOR)—CH$_2$—SH.

Passing the partially protected oligopeptide released from the capture support over a hydrophobic chromatography column results in retention of the Fmoc-bearing species. The Fmoc group is then removed by treatment with base.

Alternatively, a monomer having the structure Fmoc-NH—CH(CH$_2$—S—CH$_2$—φ)—COOH as the first residue is coupled to the solid support. After peptide assembly and deprotection the resultant Fmoc-NH-peptide-CO—NH—CH(COOR)—CH$_2$—SH can be captured and released as described above.

EXAMPLE 6

Preparation and Purification of a Peptoid Having A C-Terminus Carboxyhydrazide and an N-Terminus Capture Moiety Submonomer Peptoid Synthesis: The oligopeptoid is synthesized on a Wang-type support H$_2$N—NH—CO—O—C(CH$_3$)$_2$—(CH$_2$)$_2$—φ-Polymer. Elongation of the oligopeptoid using monomer units Br—CH$_2$—COOH and R$_1$—NH$_2$ is carried out as described in Zuckermann et al. (1992) *J. Am. Chem. Soc.* 114:10646–10647, wherein R represents a side chain substituent. The final immobilized oligopeptoid has the structure R$_{(n+1)}$—NH—CH—CO—[N(R$_n$)—CO]$_n$—NH—NH—CO—O—C(CH$_3$)$_2$—(CH$_2$)$_2$—φ-Polymer. Additional synthetic procedures well known to those of skill in the art are used to add a special linker, if required, and a capture moiety ("CM") to yield CM—NH—(CH$_2$)$_2$—S—(CH$_2$)$_2$—O—CO—N(R$_{(n+1)}$)—CO[N(R$_n$)—CO]$_n$—NH—NH—CO—O—C(CH$_3$)$_2$—(CH$_2$)$_2$—φ-Polymer. Cleavage of the crude mixture in the form of CM—NH—(CH$_2$)$_2$—S—(CH$_2$)$_2$—O—CO-Peptoid-CO—NH—NH$_2$ is effected as described in Example 4.

Purification: The CM—NH—(CH$_2$)$_2$—S—(CH$_2$)$_2$—O—CO-Peptoid-CO—NH—NH$_2$ is captured on a capture support bearing an aldehyde moiety to yield CM—NH—(CH$_2$)$_2$—S—(CH$_2$)$_2$—O—CO-peptide-CO—NH—N=CH-CaptureSupport. Release of the bound oligopeptide from the capture support in the same form as attached is achieved by cleaving CO—NH—N= via exchange with formaldehyde (Teitelbaum, supra). Alternatively, the free acid form of the bound oligopeptide is released by direct oxidation and hydrolysis (Barton et al., supra), as described herein in Example 3.

The partially protected oligopeptoid bearing the Capture Moiety released from the capture support is captured using hydrophobic chromatography, when CM is, for example, Fmoc, or a support medium bearing a moiety with which the Capture Moiety can specifically interact, e.g., if CM is biotin, the solid support will bear an avidin moiety, if CM is His$_6$, the solid support will bear an Ni—NTA moiety, or the like. Release from the capture support to yield the purified oligopeptide is achieved by oxidation followed by treatment with base.

What is claimed is:

1. A method for preparing a purified oligomer segment of interest, comprising:

(a) providing a support-bound oligomer selected from the group consisting of oligonucleotides and oligopeptides having a first selectably cleavable linkage, a second selectably cleavable linkage and a third selectably cleavable linkage, wherein the oligomer segment of interest is flanked by the second and third selectably cleavable linkages, and further wherein a first capture moiety is present at the free terminus of the oligomer and a second capture moiety is present between the first and third selectably cleavable linkages;

(b) cleaving the first selectably cleavable linkage to release the oligomer from the support;

(c) incubating the released oligomer with a first capture medium that selectively retains the released oligomer by binding to the first capture moiety, to form a first capture medium-oligomer complex;

(d) cleaving the second selectably cleavable linkage;

(e) incubating the oligomeric product of step (d) with a second capture medium that selectively binds to the second capture moiety, to form a second capture medium-oligomer complex; and (f) cleaving the third selectably cleavable linkage to provide the oligomer segment of interest in purified form.

2. The method of claim 1, wherein the oligomer is an oligonucleotide.

3. The method of claim 1, wherein the oligomer is an oligopeptide.

4. The method of claim 2, wherein the first capture medium and the second capture medium are independently selected from the group consisting of reverse phase chromatography medium, a hydrophobic interaction chromatography medium, and combinations thereof.

5. The method of claim 2, wherein the first capture moiety comprises a 5'-thiol or a 5'-dialdehyde.

6. The method of claim 2, wherein the second capture moiety comprises a 5'-thiol or a 5'-dialdehyde.

7. The method of claim 2, wherein the third selectably cleavable linkage is selected from the group consisting of (a) $N^4$—(DMT—O—$R^5$)-2',3'—O-benzoyl-riboNu$^1$, in which $R^5$ is lower alkylene, arylene, aralkylene, or alkarylene, and riboNu$^1$ is 5'-riboadenine, 5'-ribothymidine, 5'-riboguanine, 5'-ribocytidine or 5'-ribouridine, (b) —O—$R^6$—O—Si($R^7$)($R^8$)—O—Si($R^9$)($R^{10}$)-5'—O, wherein $R^6$, $R^7$, $R^8$, $R^9$, $R^{10}$ are independently lower alkyl, aryl, aralkyl, or alkaryl, and (c) an abasic site having the structural formula

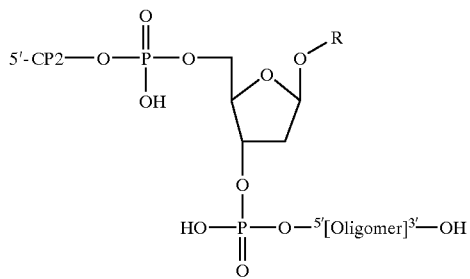

wherein:

CP2 is a 5'-terminal capture moiety; and

R is selected from the group consisting of 2-nitrobenzyl, 4-penten-1-yl, —$CH_2CH_2S\phi$, —$CH_2CH_2Si(CH_3)_3$, —$P(O)O^-{}_2$, —$CH_2CH_2$—$C_6H_4$—$NO_2$, and

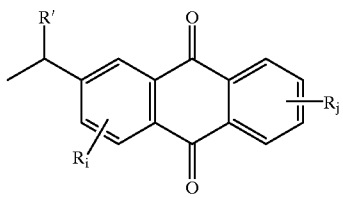

in which R' is hydrogen, aryl, or aralkyl, the $R_i$ may be the same or different and are selected from the group consisting of amino, nitro, halogeno, hydroxyl, lower alkyl and lower alkoxy, the $R_j$ may be the same or different and are selected from the group consisting of amino, nitro, halogeno, hydroxyl, lower alkyl and lower alkoxy, i is zero, 1, 2 or 3, and j is zero, 1, 2, 3 or 4.

8. The method of claim 7, wherein the third selectably cleavable linkage is —O—$R^6$—O—Si($R^7$)($R^8$)—O—Si($R^9$)($R^{10}$)-5'—O.

9. The method of claim 8, wherein the third selectably cleavable linkage is —O—$(CH_2)_2$—O—Si($CH(CH_3)_2$)$_2$—O—Si($CH(CH_3)_2$)$_2$-5'—O.

10. The method of claim 2, wherein the second selectably cleavable linkage is selected from the group consisting of $N^4$-(phosphoryl-6-oxyhexyl)cytidine, 2',3'-isopropylidine-$N^4$-(phosphoryl-6-oxyhexyl)cytidine, —P—O-alkylene-S-alkylene-O—p—, $Nu^2$—$R^{11}$—O—p—NH—$R^{12}$, allyl phosphate linkers, —$Nu^2$—3'—O—Si($R^{13}$)($R^{14}$)—O—Si($R^{15}$)($R^{16}$)—O—, $Nu^2$—O—Si($R^{18}$)($R^{19}$)-2-O—$Nu^2$—O—Si($R^{21}$)($R^{22}$)—$R^{23}$—Si($R^{24}$)($R^{25}$)—O—, 2'-O—PG-ribonucleotide, $Nu^2$—O—$R^{27}S$—, $Nu^2$—O—$R^{29}$—O—$R^{30}$($NO_2$), and $Nu^2$—O—p—O—$R^{31}$—NH(allyloxycarbonyl)-O—, wherein $Nu^2$ is the terminal 3' nucleotide of the oligomer, $R^{11}$ is a nucleoside, $R^{12}$, $R^{13}$, $R^{14}$, $R^{15}$, $R^{16}$, $R^{18}$, $R^{19}$, $R^{21}$, $R^{22}$, $R^{23}$, $R^{24}$, $R^{25}$, $R^{27}$ are independently lower alkyl, aryl, aralkyl, or alkaryl $R^{29}$ and $R^{31}$ are lower alkyl, and $R^{30}$ is aryl, aralkyl, or alkaryl.

11. The method of claim 2, wherein the second selectably cleavable linkage is selected from the group consisting of $N^4$-(phosphoryl-6-oxyhexyl)cytidine, 2',3'-isopropylidine-$N^4$-(phosphoryl-6-oxyhexyl)cytidine, —P—O-alkylene$_1$-S-alkylene$_2$-O—p—, in which at least one of alkylene$_1$ and alkylene$_2$ is ethylene, $R^{11}$—O—p—NH—$R^{12}$, wherein $R^{11}$ is a nucleoside and $R^{12}$ is alkyl, aryl, aralkyl or alkaryl, allyl phosphate linkers, —$Nu^2$-3'—O—Si($R^{13}$)($R^{14}$)—O—Si($R^{15}$)($R^{16}$)—O—$R^{17}$, wherein $Nu^2$ is the terminal 3' nucleotide of the oligomer, $R^{13}$, $R^{14}$, $R^{15}$ and $R^{16}$ are independently lower alkyl, aryl, aralkyl or alkaryl and $R^{17}$ is a capture moiety, —$Nu^2$—O—Si($R^{18}$)($R^{19}$)—2—O—$R^{20}$, wherein $Nu^2$ is as defined above, $R^{18}$ and $R^{19}$ are independently lower alkyl, aryl, aralkyl or alkaryl and $R^{20}$ is a capture moiety, $Nu^2$—O—Si($R^{21}$)($R^{22}$)—$R^{23}$—Si($R^{24}$)($R^{25}$)—O—$R^{26}$, wherein $Nu^2$ is the terminal 3' nucleotide of the oligomer, $R^{21}$, $R^{22}$, $R^{23}$, $R^{24}$ and $R^{25}$ are independently lower alkyl, aryl, aralkyl, or alkaryl and $R^{26}$ is a capture moiety, 2'-O—PG-ribonucleotide, in which PG is t-butyl-dimethyl-silyl, phosphate, 1-methoxycyclohexyl ether, methylthiomethyl ether, siloxymethyl ether, $Nu^2$—O—$R^{27}S$—$R^{28}$, wherein $Nu^2$ is the terminal 3' nucleotide of the oligomer, $R^{27}$ is lower alkyl, aryl, aralkyl, or alkaryl, and $R^{28}$ is a capture moiety, $Nu^2$—O—$R^{29}$—O—$R^{30}(NO_2)$, wherein $Nu^2$ is the terminal 3' nucleotide of the oligomer, $R^{29}$ is lower alkyl and $R^{30}$ is aryl, aralkyl, or alkaryl, linkers derived from alkyldiolamines wherein the derivative has the formula $Nu^2$—O—p—O—$R^{31}$—NH(allyloxycarbonyl)—O—, wherein $Nu^2$ is the terminal 3' nucleotide of the oligomer, and $R^{31}$ is lower alkyl, and selectably cleavable abasic sites having the formula

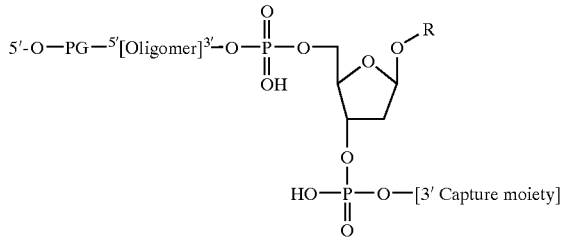

wherein
R is selected from the group consisting of 2-nitrobenzyl, 4-penten-1-yl, —$CH_2CH_2S\phi$, —$CH_2CH_2Si(CH_3)_3$, —$P(O)O^-_2$, —$CH_2CH_2$—$C_6H_4$—$NO_2$, and

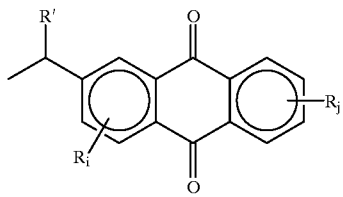

in which R' is hydrogen, aryl, or aralkyl, the $R_i$ may be the same or different and are selected from the group consisting of amino, nitro, haloeno, hydroxyl, lower alkyl and lower alkoxy, the $R_j$ may be the same or different and are selected from the group consisting of amino, nitro, halogeno, hydroxyl, lower alkyl and lower alkoxy, i is zero, 1, 2 or 3, and j is zero, 1, 2, 3 or 4.

12. The method of claim 2, wherein the first capture moiety is selected from the group consisting of a 3'-thiol moiety, a 3'-bromoacetyl moiety, a 3'-malimido moiety, a 3'-dialdehyde moiety, a hydrazide moiety, a (6-histaminylpurine)$_6$ moiety, a diol moiety, a dinitrophenyl moiety, and a Diels-Alder moiety.

13. The method of claim 2, wherein the second capture moiety is selected from the group consisting of a 3'-thiol moiety, a 3'-bromoacetyl moiety, a 3'-malimido moiety, a 3'-dialdehyde moiety, a hydrazide moiety, a (6-histaminylpurine)$_6$ moiety, a diol moiety, a dinitrophenyl moiety, and a Diels-Alder moiety.

14. A support-bound oligomer selected from the group consisting of oligonucleotides and oligopeptides having the structural formula (I)

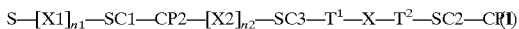

wherein:
$T^1$ and $T^2$ represent first and second oligomer termini, respectively;
S represents a solid support;
X represents an oligomer segment of interest;
X1 and X2 are monomers or oligomeric segments;
n1 and n2 are independently zero or 1;
SC1 represents a first selectably cleavable linkage;
SC2 represents a second selectably cleavable linkage;
SC3 represents a third selectably cleavable linkage;
CP1 represents a first capture moiety; and
CP2 represents a second capture moiety.

15. The support-bound oligomer of claim 14, wherein the oligomer is an oligonucleotide and wherein:
$T^1$ and $T^2$ are the 3' and 5' termini, respectively;
CP1 represents a 5'-terminal capture moiety;
SC2 represents a 5' cleavable linker;
SC3 represents a 3' cleavable linker;
CP2 represents a 3'-capture moiety;
SC1 represents a synthesis release moiety; and
S represent the solid synthesis support.

16. A method for preparing a purified oligomer segment of interest, comprising:
(a) providing a support-bound oligomer selected from the group consisting of oligonucleotides and oligopeptides having the structural formula (I)

wherein:
$T^1$ and $T^2$ represent first and second oligomer termini, respectively;
S represents a solid support;
X represents an oligomer segment of interest;
X1 and X2 are monomers or oligomeric segments;
n1 and n2 are independently zero or 1;
SC1 represents a first selectably cleavable linkage;
SC2 represents a second selectably cleavable linkage;
SC3 represents a third selectably cleavable linkage;
CP1 represents a first capture moiety; and
CP2 represents a second capture moiety;
(b) cleaving the first selectably cleavable linkage to release the oligomer from the support;
(c) incubating the released oligomer with a first capture medium that selectively retains the released oligomer by binding to the first capture moiety, to form a first capture medium-oligomer complex;
(d) cleaving the second selectably cleavable linkage;
(e) incubating the oligomeric product of step (d) with a second capture medium that selectively binds to the second capture moiety, to form a second capture medium-oligomer complex; and
(f) cleaving the third selectably cleavable linkage to provide the oligomer segment of interest in purified form.

* * * * *

UNITED STATES PATENT AND TRADEMARK OFFICE
CERTIFICATE OF CORRECTION

PATENT NO.    : 6,472,522 B1
DATED         : October 29, 2002
INVENTOR(S)   : Horn et al.

It is certified that error appears in the above-identified patent and that said Letters Patent is hereby corrected as shown below:

Column 93,
Line 13, please delete "haloeno" and replace with -- halogeno --.

Column 94,
Line 10, please delete "represent" and replace with -- represents --.

Signed and Sealed this

Twenty-second Day of July, 2003

JAMES E. ROGAN
*Director of the United States Patent and Trademark Office*